(12) United States Patent
Zhou

(10) Patent No.: US 7,259,240 B2
(45) Date of Patent: Aug. 21, 2007

(54) PRIMATE PROKINETICIN RECEPTOR POLYPEPTIDES

(75) Inventor: Qun-Yong Zhou, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 292 days.

(21) Appl. No.: 10/977,113

(22) Filed: Oct. 29, 2004

(65) Prior Publication Data

US 2005/0143287 A1    Jun. 30, 2005

Related U.S. Application Data

(60) Provisional application No. 60/516,115, filed on Oct. 31, 2003.

(51) Int. Cl.
*C07K 14/705* (2006.01)
(52) U.S. Cl. .................................... 530/350
(58) Field of Classification Search ................ None
See application file for complete search history.

(56) References Cited

U.S. PATENT DOCUMENTS 5,891,720 A * 4/1999 Moore et al. ............... 435/325
2004/0235732 A1* 11/2004 Zhou et al. .................. 514/12
2006/0019338 A1* 1/2006 Zhou .......................... 435/69.1

OTHER PUBLICATIONS

Li 2001. Molecular Pharmacology 59:692-698.*
Lin 2002. Journal of Biological Chemistry 277:19276-19280.*
Gehlert et al., "Cloning and Characterization of Rhesus Monkey Neuropeptide Y Receptor Subtypes" *Peptides*, 22:343-350, Elsevier Science Inc. (2001).
Masuda et al., "Isolation and Identification of EG-VEGF/Prokineticins as Cognate Ligands for Two Orphan G-Protein-Coupled Receptors," *Biochemical and Biophysical Research Communications*, 293:396-402, Elsevier Science (USA) (2002).

* cited by examiner

*Primary Examiner*—Robert C. Hayes
*Assistant Examiner*—Daniel E. Kolker
(74) *Attorney, Agent, or Firm*—DLA Piper US LLP

(57) ABSTRACT

The invention provides an isolated squirrel monkey prokineticin receptor 2 (PKR2) polypeptide containing the amino acid sequence referenced as SEQ ID NO:2. The invention also provides an isolated chimpanzee PKR2 containing the amino acid sequence referenced as SEQ ID NO:4. Also provided are methods of identifying PKR2 agonists and antagonists using the squirrel monkey PKR2 polypeptide. Additionally, the invention provides an isolated rhesus monkey PK2 polypeptide containing the amino acid sequence referenced as SEQ ID NO:6. Nucleic acid molecules encoding the disclosed polypeptides further are provided by the invention.

2 Claims, 13 Drawing Sheets

A

Squirrel Monkey PKR2 nucleotide sequence (SEQ ID NO:1)

ATGGCAGCCCAGAATGGAAACACCAGTTTTGCACCCAACTTTAATCCACCCCAAGACCATGCCTCCTCCCTCTCCTTCAA
CTTCAGTTATGGTGATTACGACCTCCCTATGGATGAGGATGAGGACATGACCAAGACCCGGACCTTCTTTGCAGCCAAGA
TTGTCATCGGCATTGCACTGGCAGGCATCATGCTGGTCTGTGGTGTCGGTAACTTTGTCTTTATCGCTGCCCTCACCCGC
TATAAGAAGCTGCGCAACCTCACCAATCTGCTCATTGCCAACCTGGCCATCTCCGACTTCCTGGTGGCCATCATCTGCTG
CCCCTTTGAGATGGACTACTATGTGGTCCGGCAGCTCTCCTGGGAGCATGGCCACGTGCTCTGTGCCTCTGTCAACTACC
TGCGCACCGTCTCCCTCTACGTCTCCACCAATGCCTTGCTGGCCATCGCCATTGACAGATATCTCGCCATTGTTCACCCC
TTGAAACCAAGGATGAATTATCAAACGGCCTCCTTCCTGATCGCCTTGGTCTGGATGGTATCCATTCTCATTGCCATCCC
ATCAGCCTACTTTGCAACAGAAACCGTCCTCTTTATTGTCAAGAGCCAGGAGAAGATCTTCTGTGGCCAGATCTGGCCCG
TGGATCAGCAGCTCTACTACAAGTCCTACTTCCTCTTCATCTTTGGTGTGGAGTTCGTGGGTCCTGTGGTCACCATGACC
CTGTGCTACGCCAGGATTTCCCAGGAGCTCTGGTTCAAGGCAGTCCCTGGGTTCCAGACAGAGCAGATCCGTAAGCGGCT
GCGCTGCCGCAGGAAGACAGTCCTGGTGCTCATGTGCATCCTCATGGCCTACGTGCTATGCTGGGCACCCTTCTATGGTT
TCACCATCGTACGCGACTTCTTCCCCACCGTGTTCGTAAAGGAAAAGCACTACCTCACTGCCTTCTACGTGGTCGAGTGC
ATCGCCATGAGCAACAGCATGATCAACACCGTGTGCTTCGTGACGGTCAAGAACAACACCATGAAGTATTTCAAGAAGAT
GATGCTGCTGCACTGGCGTCCCTCCCAGCGGGGGAGCAAGTCCAGTGCCGACCTTGACCTTAAGACGAACGGGGTGCCTG
CCACGGAAGAGGTGGACTGTATCAGGCTGAAGTGA

B

Squirrel Monkey PKR2 amino acid sequence (SEQ ID NO:2)

MAAQNGNTSFAPNFNPPQDHASSLSFNFSYGDYDLPMDEDEDMTKTRTFFAAKIVIGIALAGIMLVCGVGN
FVFIAALTRYKKLRNLTNLLIANLAISDFLVAIICCPFEMDYYVVRQLSWEHGHVLCASVNYLRTVSLYVS
TNALLAIAIDRYLAIVHPLKPRMNYQTASFLIALVWMVSILIAIPSAYFATETVLFIVKSQEKIFCGQIWP
VDQQLYYKSYFLFIFGVEFVGPVVTMTLCYARISQELWFKAVPGFQTEQIRKRLRCRRKTVLVLMCILMAY
VLCWAPFYGFTIVRDFFPTVFVKEKHYLTAFYVVECIAMSNSMINTVCFVTVKNNTMKYFKKMMLLHWRPS
QRGSKSSADLDLKTNGVPATEEVDCIRLK

Chimpanzee PKR2 nucleotide sequence (SEQ ID NO:3)

ATGGCAGCCCAGAATGGAAACACCAGTTTCGCACCCAACTTTAATCCACCGCAAGACCATGCCTCCTCCCTCTCCTTTAAC
TTCAGTTATGGTGATTATGACCTCCCTATGGATGAGGATGAGGACATGACCAAGACCCGGACCTTCCTCGCAGCCAAGAT
CGTCGTTGGCATTGCACTGGCAGGCATCATGCTGGTCTGCGGCATCGGTAACTTTGTCTTTATCGCTGCCCTCACCCGCT
ATAAGAAGTTGCGCAACCTCACCAATCTGCTCATTGCCAACCTGGCCATCTCCGACTTCCTGGTGGCCATCATCTGCTGC
CCCTTCGAGATGGACTACTACGTGGTACGGCAGCTCTCCTGGGAGCATGGCCACGTGCTCTGTGCCTCCGTCAACTACCT
GCGCACCGTCTCCCTCTACGTCTCCACCAATGCCTTGCTGGCCATCGCCATTGACAGATATCTCGCCATTGTTCACCCTT
TGAAACCACGGATGAATTATCAAACGGCCTCCTTCCTGATCGCCTTGGTCTGGATGGTGTCCATTCTCATTGCCATCCCA
TCGGCCTACTTTGCAACAGAAACCGTCCTCTTTATTGTCAAGAGCCAGGAGAAGATCTTCTGTGGCCAGATCTGGCCCGT
GGATCAGCAGCTCTACTACAAGTCCTACTTCCTCTTCATCTTTGGTGTCGAGTTCGTGGGCCCTGTGGTCACCATGACCC
TGTGCTATGCCAGGATCTCCCGGGAGCTCTGGTTCAAGGCAGTCCCTGGGTTCCAGACGGAGCAGATTCGCAAGCGGCTG
CGCTGCCGCAGGAAGACGGTCCTGGTGCTCATGTGCATTCTCACGGCCTATGTGCTGTGCTGGGCACCCTTCTACGGTTT
CACCATCGTTCGTGACTTCTTCCCCACTGTGTTCGTGAAGGAAAAGCACTACCTCACTGCCTTCTACGTGGTCGAGTGCA
TCGCCATGAGCAACAGCATGATCAACACCGTGTGCTTCGTGACGGTCAAGAACAACACCATGAAGTACTTCAAGAAGATG
ATGCTGCTGCACTGGCGTCCCTCCCAGCGGGGGAGCAAGTCCAGTGCCGACCTTGACCTCAGAACCAACGGGGTGCCCGC
CACAGAAGAGGTGGACTGTATCAGGCTGAAGTGA

B

Chimpanzee PKR2 amino acid sequence (SEQ ID NO:4)

MAAQNGNTSFAPNFNPPQDHASSLSFNFSYGDYDLPMDEDEDMTKTRTFLAAKIVVGIALAGIMLVCGIGN
FVFIAALTRYKKLRNLTNLLIANLAISDFLVAIICCPFEMDYYVVRQLSWEHGHVLCASVNYLRTVSLYVS
TNALLAIAIDRYLAIVHPLKPRMNYQTASFLIALVWMVSILIAIPSAYFATETVLFIVKSQEKIFCGQIWP
VDQQLYYKSYFLFIFGVEFVGPVVTMTLCYARISRELWFKAVPGFQTEQIRKRLRCRRKTVLVLMCILTAY
VLCWAPFYGFTIVRDFFPTVFVKEKHYLTAFYVVECIAMSNSMINTVCFVTVKNNTMKYFKKMMLLHWRPS
QRGSKSSADLDLRTNGVPATEEVDCIRLK

Figure 2

Comparison of Primate PKR2 Amino Acid Sequences

Human (SEQ ID NO:7)
MAAQNGNTSFTPNFNPPQDHASSLSFNFSYGDYDLPMDEDEDMTKTRTFFAAKIVIGIALAGIMLVCGIGN
S. monkey (SEQ ID NO:2)
MAAQNGNTSFAPNFNPPQDHASSLSFNFSYGDYDLPMDEDEDMTKTRTFFAAKIVIGIALAGIMLVCGVGN
M. fasc. (SEQ ID NO:8)
MAAQNGNTSFAPNFNPPQDHASSLSFNFSYGDYDLPMDEDEDMTKTRTFFAAKIVIGIALAGIMLVCGIGN
Chimpanzee (SEQ ID NO:4)
MAAQNGNTSFAPNFNPPQDHASSLSFNFSYGDYDLPMDEDEDMTKTRTFLAAKIVVGIALAGIMLVCGIGN Human (Cont.)
FVFIAALTRYKKLRNLTNLLIANLAISDFLVAIICCPFEMDYYVVRQLSWEHGHVLCASVNYLRTVSLYVS
S. monkey (Cont.)
FVFIAALTRYKKLRNLTNLLIANLAISDFLVAIICCPFEMDYYVVRQLSWEHGHVLCASVNYLRTVSLYVS
M. fasc. (Cont.)
FVFIAALTRYKKLRNLTNLLIANLAISDFLVAIICCPFEMDYYVVRQLSWEHGHVLCASVNYLRTVSLYVS
Chimpanzee (Cont.)
FVFIAALTRYKKLRNLTNLLIANLAISDFLVAIICCPFEMDYYVVRQLSWEHGHVLCASVNYLRTVSLYVS Human (Cont.)
TNALLAIAIDRYLAIVHPLKPRMNYQTASFLIALVWMVSILIAIPSAYFATETVLFIVKSQEKIFCGQIWP
S. monkey (Cont.)
TNALLAIAIDRYLAIVHPLKPRMNYQTASFLIALVWMVSILIAIPSAYFATETVLFIVKSQEKIFCGQIWP
M. fasc. (Cont.)
TNALLAIAIDRYLAIVHPLKPRMNYQTASFLIALVWMVSILIAIPSAYFATETVLFIVKSQEKIFCGQIWP
Chimpanzee (Cont.)
TNALLAIAIDRYLAIVHPLKPRMNYQTASFLIALVWMVSILIAIPSAYFATETVLFIVKSQEKIFCGQIWP Human (Cont.)
VDQQLYYKSYFLFIFGVEFVGPVVTMTLCYARISRELWFKAVPGFQTEQIRKRLRCRRKTVLVLMCILTAY
S. monkey (Cont.)
VDQQLYYKSYFLFIFGVEFVGPVVTMTLCYARISQELWFKAVPGFQTEQIRKRLRCRRKTVLVLMCILMAY
M. fasc. (Cont.)
VDQQLYYKSYFLFIFGVEFVGPVVTMTLCYARISRELWFKAVPGFQTEQIRKRLRCRRKTVLVLMCILTAY
Chimpanzee (Cont.)
VDQQLYYKSYFLFIFGVEFVGPVVTMTLCYARISRELWFKAVPGFQTEQIRKRLRCRRKTVLVLMCILTAY Human (Cont.)
VLCWAPFYGFTIVRDFFPTVFVKEKHYLTAFYVVECIAMSNSMINTVCFVTVKNNTMKYFKKMMLLHWRPS
S. monkey (Cont.)
VLCWAPFYGFTIVRDFFPTVFVKEKHYLTAFYVVECIAMSNSMINTVCFVTVKNNTMKYFKKMMLLHWRPS
M. fasc. (Cont.)
VLCWAPFYGFTIVRDFFPTVFVKEKHYLTAFYVVECIAMSNSMINTVCFVTVKNNTMKYFKKMMLLHWRPS
Chimpanzee (Cont.)
VLCWAPFYGFTIVRDFFPTVFVKEKHYLTAFYVVECIAMSNSMINTVCFVTVKNNTMKYFKKMMLLHWRPS Human    (Cont.)    QRGSKSSADLDLRTNGVPTTEEVDCIRLK
S. monkey (Cont.)   QRGSKSSADLDLKTNGVPATEEVDCIRLK
M. fasc.  (Cont.)   QWGSKSSAELDLRTNGVPATEEVDCIRLK
Chimpanzee (Cont.)  QRGSKSSADLDLRTNGVPATEEVDCIRLK

Rhesus Monkey PK2 nucleotide sequence (SEQ ID NO:5)

CGCCATGAGGAGCCTGTGCTGCGCCCCACTCCTGCTCCTCCTGCTGCTGC
CGCCGCTGCTGCTCACGCCCCGCGTCGGGGACGCCGCCGTGATCACCGGG
GCTTGTGACAAGGACTCCCAATGTGGTGGAGGCATGTGCTGTGCTGTCAG
TATCTGGGTTAAGAGCATAAGGATTTGCACACCTATGGGCAAACTGGGAG
ACAGCTGCCATCCACTGACTCGTAAAGTTCCATTTGTTGGGCGGAGGATG
CATCACACTTGCCCATGTCTGCCAGGCTTGGCCTGTTTACGGACTTCATT
TAACCGATTTATTTGTTTAGCCCGAAAGTAATCGCTTTAAAGTAGAAACC
AAATGTGAATAGCCACATCTTATCTGTAAAGTCTTACTTGTGATTGTGCC
AAACAAAAAATGTGCCAGAAAGAAATGCTTTTGCTTCCTCAACTTTCCAA
GTAACTTTTTATCTTTGAGTTTTAAATGATTTTTTTTTAATCGGGAAT
TTTACTTTTGGATAGAAATATAAAGTGTAAGGCATTGTGGAACTGGTTCT
CATTTCCCTGTTTGTGTTTTGGTTTGGTTTGGCTTTTTTCTTAAATGTCA
AAAACATACCCATTTTCACAAAAATGAGGAAAATAGGAATTTGATATTTT
GTTAGAGAAACTTTTTTTTTCCTCACCATCCCAAGCCCCATTTGTGCCCC
GCCACACCATACCATACATACATACATACATACATACATACATACATACA
ACTTTTGGTCCCTTGCCTCTTCCACCTCAAAGAATTTCAAGGCCCTTACC
TTACTTTATTTTTCTCCATTTCTCTTCCCTGCTCTTGCATTTTAAAGTGG
TAGGTTTATCTCTTTGAGTTTGATGGCAGAATCGCTGATGGGAATCCAGC
TTTTTGCCGGCTATTTAAATAGTGAAAAGAGTTTATATGTGAACTTGACA
CTCCAAACTCCTCTCATGGCGTGGACGCTGGGAGTGCTGCCGGACCCTTC
CTAAACCTGTCACTCAAGAGGACTTCGGCTCTGCTGTTGGGCTGGTGTGT
GGACAGAAGGAATGGAAAGCTAAATTAATTTAGTCCAGATTTCTAGGTTT
GGGTTTTCTAAAAATGAAAGATTACGTTTACTTCTTTTTCTTTTTATAA
AGTTTTTTTTTCTTAGTCTCCTACTTAGAGATATTCTAGAAAATGTCACT
TGAA

[Coding: nucleotides 5-329]

B

Rhesus Monkey PK2 amino acid sequence (SEQ ID NO:6)

<u>MRSLCCAPLLLLLLLPPLLLT</u>PRVGDAAVITGACDKDSQCGGGMCCAVSI
WVKSIRICTPMGKLGDSCHPLTRKVPFVGRRMHHTCPCLPGLACLRTSFN
RFICLARK

[Signal peptide underlined]

Figure 4

Comparison of PK2 Amino Acid Sequences

Human PK2 (SEQ ID NO:9)
AVITGACDKDSQCGGGMCCAVSIWVKSIRICTPMGKLGDSCHPLTRKVPFFGRRMHHTCPCLPG
Rhesus PK2 (SEQ ID NO:6)
AVITGACDKDSQCGGGMCCAVSIWVKSIRICTPMGKLGDSCHPLTRKVPFVGRRMHHTCPCLPG
Mouse/rat PK2 (SEQ ID NO:10)
AVITGACDKDSQCGGGMCCAVSIWVKSIRICTPMGQVGDSCHPLTRKVPFWGRRMHHTCPCLPG Human PK2 (Cont.)      LACLRTSFNRFICLAQK
Rhesus PK2 (Cont.)     LACLRTSFNRFICLARK
Mouse/rat PK2 (Cont.)  LACLRTSFNRFICLAR

Figure 5

HUMAN PK1 (SEQ ID NO:11)
AVITGACERDVQCGAGTCCAISLWLRGLRMCTPLGREGEECHPGSHKVPFFRKRKHHTCPCL
PN LLCSRFPDGRYRCSMDLKNINF

MOUSE PK1 (SEQ ID NO:12)
AVITGACERDIQCGAGTCCAISLWLRGLRLCTPLGREGEECHPGSHKIPFLRKRQHHTCPCS
PS LLCSRFPDGRYRCFRDLKNANF

TOAD Bv8 (SEQ ID NO:13)
AVITGACDKDVQCGSGTCCAASAWSRNIRFCIPLSGEDCHPASHKVPYDGKRLSSLCPCKSG
LT CSKSGEKFKCS

FROG Bv8(SEQ ID NO:14)
AVITGACDKDVQCGSGTCCAASAWSRNIRFCIPLGNSGEDCHPASHKVPYDGKRLSSLCPCK
SG LTCSKSG-EKFKCS

SNAKE MIT1 (SEQ ID NO:15)
AVITGACERDLQCGKGTCCAVSLWIKSVRVCTPVGTSGEDCHPASHKIPFSGQRMHHTCPCA
PN LACVQTSPKKFKCLSK human PK1-PK2 Chimera 12 (SEQ ID NO:16)
AVITGACERDVQCGAGTCCAISLWLRGLRMCTPLGREGEECHPGSHKVPFFGRRMHHTCPCL
PGLACLRTSFNRFICLAQK human PK2-PK1 Chimera (SEQ ID NO:17)
AVITGACDKSQCGGGMCCAVSIWVKSIRICTPMGKLGDSCHPLTRKVPFFRKRKHHTCPCL
PNLLCSRFPDGRYRCSMDLKNINF

Figure 6

Figure 8. Comparison of the Functional Activity of Recombinant Chimpanzee and Human PKR2 expressed in CHO cells. Y-axis: RLU (relative light units).
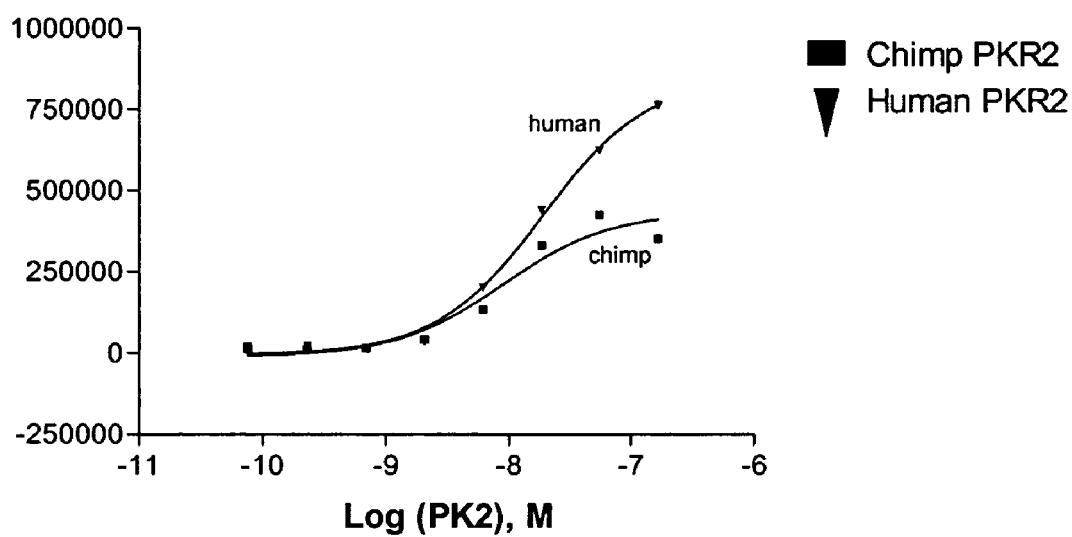

Figure 9. Nucleotide Sequence of Rhesus Monkey PK1 (SEQ ID NO:29)

```
CCTTCAAGTGACCATGAGAGGTGCCACGCTAGTCTCAATCATGTTCCTCCTAGTAACTGTGTCTGACTGTGCTGTGATCACAGGG
GCCTGTGAGCGGGATGTCCAGTGTGGGGCAGGCACCTGCTGTGCCATCAGCCTGTGGCTTCGAGGGCTGCGGATGTGTACCCCGC
TGGGGCGGGAAGGCGAGGAGTGCCATCCTGGCAGCCACAAGGTCCCCTTCTTTAGGAAACGCAAGCACCATACCTGTCCTTGCTC
ACCCAACCTGCTGTGCTCCAGGTTCCCAGACGGCAGGTACCGCTGCTCCATGGACTTGAAGAACATCAATTTTTAGGCGCTTGCC
GGGTCTCAGGATACCCACCATCCTTTTCCCCAGCACTGCCTGGATTTTTATTTGTGCCATGCAACCCAGCTCCTGTGACTCTTCC
AGTCCCTACGCTGACTACTTTGATCTCTCTTGCCTAGTACACACATATGCACACAGGGAGACATACCTCCCATCATGACGTGGTC
CCCAGGCTGGCCTGACGATGTCCCAGCTTGGAGCTGTGGTGTGAGAGATGGCCAGCCTGGTTCCCTTCCCTGCTTAGGCTGCCAG
AGAGGTGGTAAATGGCAGAGAGGACATTCCCCCTCCCCTCCCTTCCTGGGCCTGCTCTCCTTCCTGGGCCCTGTCCCTCTCCCCA
CATGTACCCCGCGGTCTGAATTGGACATTCCTGGCACAGGCTCTTGGGTGCATTGTGGGCACAGGCTCTTGGGTGCATTGAA
```

Figure 10. Predicted Amino Acid Sequence of Sequence of Rhesus Monkey PK1 (SEQ ID NO:30 )

<u>MRGATLVSIMFLLVTVSDCAV</u>ITGACERDVQCGAGTCCAISLWLRGLRMCTPLGREGEECHPGSHKVPFFRKRK
HHTCPCLPNLLCSRFPDGRYRCSMDLKNINF

*Signal peptide (1-19) is underlined [ mature PK2 protein: 20-125]*

Figure 11. Alignment of the Amino Acid Sequences for Rhesus Monkey, Human PK1 and Human Isoform PK1

Rhesus PK1 (SEQ ID NO:30)
Human PK1 (SEQ ID NO:11)
Human PK1 isoform (Takeda) (SEQ ID NO:31)

```
MRGATLVSIMFLLVTVSDCAVITGACERDVQCGAGTCCAISLWLRGLRMCTPLGREGEECHPGSHKVPFF
MRGATRVSIMLLLVTVSDCAVITGACERDVQCGAGTCCAISLWLRGLRMCTPLGREGEECHPGSHKIPFF
MRGATRVSIMLLLVTVSDCAVITGACERDVQCGAGTCCAISLWLRGLRMCTPLGREGEECHPGSHKVPFF

RKRKHHTCPCLPNLLCSRFPDGRYRCSMDLKNINF
RKRKHHTCPCLPNLLCSRFPDGRYRCSMDLKNINF
RKRKHHTCPCLPNLLCSRFPDGRYRCSMDLKNINF
```

Figure 12. Rhesus Monkey PKR1 Nucleotide sequence (SEQ ID NO:34 )

```
ATGGAGACCACCATGGGGTTCATGGATGACAATGCCACCAACACCTCCACCAGCTTCCTTTCTGCGCTCAACCCTCATGGAGCCC
ATGCCGCTTCCTTCCCATTCAACTTCAGCTATGGTGACTATGATATGCCTTTGGATGAAGATGAGGATGTGACCAATTCCCGGAC
ATTCTTTGCTGCCAAGATTGTCATTGGGATGGCCCTGGTGGGCATCATGCTGGTCTGTGGCATTGGCAACTTCGTCTTTATCGCT
GCTCTGGTCCGCTACAAGAAACTGCGCAATCTCACCAACCTGCTCATCGCCAACCTGGCCATCTCGGATTTCCTGGTGGCCATTG
TCTGCTGCCCCTTTGAGATGGACTACTATGTGGTGCGCCAGCTCTCCTGGGAGCACGGCCACATCCTGTGCACCTCTGTCAACTA
CCTGCGCACTGTCTCTCTCTATGTCTCCACCAATGCCCTGCTGGCCATCGCCATTGACAGGTATCTGGCTATTGTCCACCCGCTG
AGACCACGGATGAAGTGCCAAACAGCCACTGGCCTGATTGCCTTGGTGTGGACGGTGTCCATCCTGATCGCCATCCCTTCCGCCT
ACTTCACCACCGAGACGGTCCTCGTCATTGTCAGGAGCCAGGAAAAGATCTTCTGCGGCCAGATCTGGCCTGTTGACCAGCAGCT
GTACTACAAGTCCTACTTCCTCTTTATCTTTGGCATTGAGTTCGTGGGCCCCGTGTTCACCATGACCCTGTGCTATGCCAGGATC
TCCCGGGAGCTCTGGTTCAAGGCGGTCCCTGGATTCCAGACCGAGCAGATCCGCAAGAGGCTGCGCTGCCGCAGGAAGACGGTCC
TGGTGCTTATGTGCATCCTCACCGCCTACGTGCTGTGCTGGGCGCCCTTCTACGGCTTCACCATCGTGCGCGACTTCTTCCCCAC
CGTGTTCGTGAAGGAGAAGCACTACCTCACTGCCTTCTACATCGTCGAGTGCATCGCCATGAGCAACAGCATGATCAACACCCTG
TGCTTCGTGACAGTCAAGAACAACACCGCCAAGTACTTCAAAAAGATCATGCTGCTCCACTGGAAGGCTTCTTACAATGGCGGTA
AGTCCAGTGCAGACCTGGACCTCAAGACAATCGGGATGCCTGCCACTGAAGAGGTGGACTGCATCAGACTAAAATAA
```

Figure 13. Predicted Amino acid sequence of Rhesus Monkey PKR1 (SEQ ID NO: 35)

```
METTMGFMDDNATNTSTSFLSALNPHGAHAASFPFNFSYGDYDMPLDEDEDVTNSRTFFAAKIVIGMALVGIML
VCGIGNFVFIAALVRYKKLRNLTNLLIANLAISDFLVAIVCCPFEMDYYVVRQLSWEHGHILCTSVNYLRTVSL
YVSTNALLAIAIDRYLAIVHPLRPRMKCQTATGLIALVWTVSILIAIPSAYFTTETVLVIVRSQEKIFCGQIWP
VDQQLYYKSYFLFIFGIEFVGPVFTMTLCYARMTRELWFKAVPGFQTEQIRKRLRCRRKTVLVLMCILTAYVLC
WAPFYGFTIVRDFFPTVFVKEKHYLTAFYIVECIAMSNSMINTLCFVTVKNNTAKYFKKIMLLHWKASYNGGKS
SADLDLKTIGMPATEEVDCIRLK
```

Figure 14. Alignment of human and Rhesus Monkey PKR1

HUMAN PKR1(SEQ ID NO:36)     METTMGFMD
RHESUS PKR1 (SEQ ID NO:35)    METTMGFMD

DNATNTSTSFLSVLNPHGAHATSFPFNFSYSDYDMPLDEDEDVTNSRTFFAAKIVIGMALVGIMLVCGIGN
DNATNTSTSFLSALNPHGAHAASFPFNFSYGDYDMPLDEDEDVTNSRTFFAAKIVIGMALVGIMLVCGIGN

FIFIAALVRYKKLRNLTNLLIANLAISDFLVAIVCCPFEMDYYVVRQLSWEHGHVLCTSVNYLRTVSLYVS
FVFIAALVRYKKLRNLTNLLIANLAISDFLVAIVCCPFEMDYYVVRQLSWEHGHILCTSVNYLRTVSLYVS

TNALLAIAIDRYLAIVHPLRPRMKCQTATGLIALVWTVSILIAIPSAYFTTETVLVIVKSQEKIFCGQIWP
TNALLAIAIDRYLAIVHPLRPRMKCQTATGLIALVWTVSILIAIPSAYFTTETVLVIVRSQEKIFCGQIWP

VDQQLYYKSYFLFIFGIEFVGPVVTMTLCYARMTRELWFKAVPGFQTEQIRKRLRCRRKTVLVLMCILTAY
VDQQLYYKSYFLFIFGIEFVGPVFTMTLCYARMTRELWFKAVPGFQTEQIRKRLRCRRKTVLVLMCILTAY

VLCWAPFYGFTIVRDFFPTVFVKEKHYLTAFYIVECIAMSNSMINTLCFVTVKNDTVKYFKKIMLLHWKAS
VLCWAPFYGFTIVRDFFPTVFVKEKHYLTAFYIVECIAMSNSMINTLCFVTVKNNTAKYFKKIMLLHWKAS

YNGGKSSADLDLKTIGMPATEEVDCIRLK
YNGGKSSADLDLKTIGMPATEEVDCIRLK

Figure 15. Comparison of Functional Activity of Rhesus Monkey and Human PKR1 Expressed in CHO Cells (calcium mobilization assay). Y-axis: RLU (relative light units).
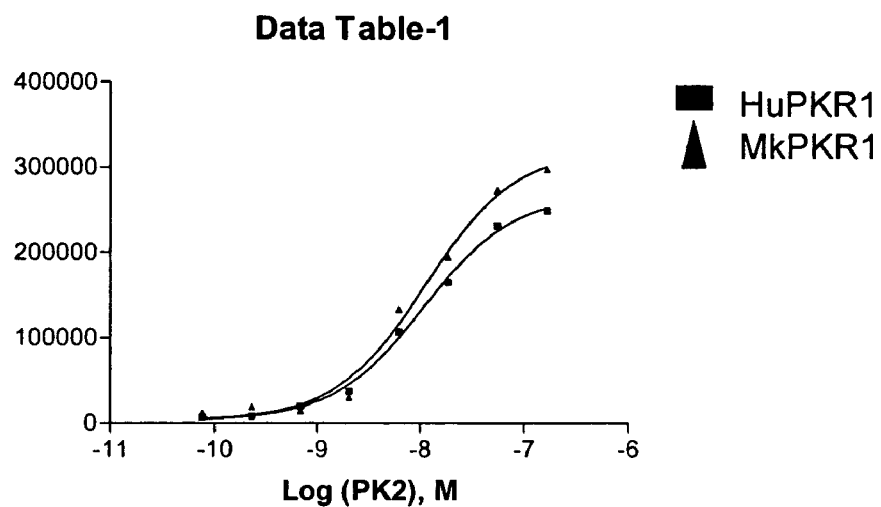

PRIMATE PROKINETICIN RECEPTOR POLYPEPTIDES

This application claims benefit of the filing date of U.S. Provisional Application No. 60/516,115, filed Oct. 31, 2003, and which is incorporated herein by reference.

BACKGROUND OF THE INVENTION

Prokineticins are secreted proteins that have roles in several biological functions, including circadian rhythm; angiogenesis; gastric contractility and motility; gastric acid and pepsinogen secretion; pain; and neurogenesis. Prokineticin 1 (PK1) and prokineticin 2 (PK2) induce cellular responses by binding to G-protein coupled receptors termed prokineticin receptor 1 (PKR1) and prokineticin receptor 2 (PKR2), resulting in activation of receptor signaling. Normal prokineticin receptor signaling contributes to the development and function of a variety of tissues in humans. If this normal signaling is disrupted, for example, due to disease, unwanted changes can occur at the cellular, tissue and whole organism level. These changes can be manifested in a variety of conditions and diseases associated with improper prokineticin receptor signaling.

To treat conditions associated with improper prokineticin receptor signaling, it is desirable to identify drugs that alter receptor activity to obtain a normal or otherwise optimal amount of signaling. Such drugs can be used, for example, to increase receptor signaling in individuals having conditions associated with insufficient prokineticin receptor activity or to decrease receptor signaling in individuals having conditions associated with excessive prokineticin receptor activity. Therefore, the identification of prokineticin receptor modulating drugs is expected to provide relief to individuals suffering from a variety of conditions attributed, at least in part, to insufficient or excessive prokineticin receptor signaling.

Thus, there exists a need to identify compounds and methods for modulating prokineticin receptor signaling. The invention satisfies this need and provides related advantages as well.

SUMMARY OF THE INVENTION

The invention provides an isolated squirrel monkey prokineticin receptor 2 (PKR2) polypeptide containing the amino acid sequence referenced as SEQ ID NO:2. Also provided by the invention is an isolated chimpanzee PKR2 containing the amino acid sequence referenced as SEQ ID NO:4. Further provided is a method of identifying a PKR2 agonist using the squirrel monkey PKR2 or chimpanzee PKR2. The method involves (a) contacting a PKR2 polypeptide containing an amino acid sequence referenced as SEQ ID NO:2 or SEQ ID NO:4 with one or more candidate compounds, and (b) identifying a compound that selectively promotes production of a PKR2 signal, said compound being characterized as an agonist of said PKR2.

The invention also provides a method of identifying a PKR2 antagonist. The method involves/contacting a PKR2 polypeptide containing an amino acid sequence referenced as SEQ ID NO:2 or SEQ ID NO:4, with one or more candidate compounds in the presence of a prokineticin, and (b) identifying a compound that selectively inhibits production of a PKR2 signal, said compound being characterized as an antagonist of said PKR2.

The invention provides an isolated nucleic acid molecule encoding a squirrel monkey PKR2 polypeptide, which contains the nucleotide sequence referenced as SEQ ID NO:1. Also provided is an isolated nucleic acid molecule encoding a chimpanzee PKR2 polypeptide, which contains the nucleotide sequence referenced as SEQ ID NO:3. Further provided are expression vectors containing a squirrel monkey or chimpanzee PKR2 nucleic acid molecule operatively linked to a promoter of gene expression. The invention also provides a host cell containing a squirrel monkey or chimpanzee PKR2 nucleic acid molecule-containing expression vector.

The invention provides an isolated rhesus monkey prokineticin 2 (PK2) polypeptide that contains the amino acid sequence referenced as SEQ ID NO:6. Also provided is an isolated nucleic acid molecule encoding the rhesus monkey PK2 polypeptide, which contains the nucleotide sequence referenced as SEQ ID NO:5. Additionally provided is an expression vector containing this nucleic acid molecule, operatively linked to a promoter of gene expression. A host cell containing the rhesus monkey PK2 expression vector is further provided.

The invention provides an isolated rhesus monkey prokineticin receptor 1 (PKR1) polypeptide containing the amino acid sequence referenced as SEQ ID NO:35. Also provided is a nucleic acid encoding the polypeptide of SEQ ID NO:35, such as a nucleic acid comprising a nucleic acid of SEQ ID NO:34. Further provided is a method of identifying a PKR1 agonist using the rhesus monkey PKR1. The method involves (a) contacting a PKR1 polypeptide containing an amino acid sequence of SEQ ID NO:35 with one or more candidate compounds, and (b) identifying a compound that selectively promotes production of a PKR1 signal, said compound being characterized as an agonist of said PKR1.

The invention provides an isolated rhesus monkey prokineticin 1 (PK1) polypeptide that contains the amino acid sequence referenced as SEQ ID NO:30. Also provided is an isolated nucleic acid molecule encoding the rhesus monkey PK1 polypeptide, which contains the nucleotide sequence referenced as SEQ ID NO:29. Additionally provided is an expression vector containing this nucleic acid molecule, operatively linked to a promoter of gene expression. A host cell containing the rhesus monkey PK1 expression vector is further provided.

Also provided is an isolated nucleic acid molecule selected from the group consisting of:

(a) the nucleotide sequence of SEQ ID NO:1, 3, 5, 29 or 34;

(b) a nucleotide sequence that encodes a polypeptide of SEQ ID NO: 2, 4, 6, 30 or 35; and (c) an allelic variant of the nucleotide sequence specified in (a) or (b).

The invention also provides a method of identifying a PKR1 antagonist. The method involves: (a) contacting a PKR1 polypeptide containing an amino acid sequence of SEQ ID NO:35 with one or more candidate compounds in the presence of a prokineticin, and (b) identifying a compound that selectively inhibits production of a PKR1 signal, said compound being characterized as an antagonist of said PKR1.

The invention provides an isolated nucleic acid molecule encoding a rhesus monkey PKR1 polypeptide, which contains the nucleotide sequence referenced as SEQ ID NO:34. Further provided are expression vectors containing a rhesus monkey nucleic acid molecule operatively linked to a promoter of gene expression. The invention also provides a host cell containing a rhesus monkey PKR1 nucleic acid molecule-containing expression vector.

BRIEF DESCRIPTION OF THE DRAWINGS

FIG. 1A shows the nucleotide sequence of squirrel monkey PKR2 (SEQ ID NO:1). FIG. 1B shows the amino acid sequence of squirrel monkey PKR2 (SEQ ID NO:2).

FIG. 2A shows the nucleotide sequence of chimpanzee PKR2 (SEQ ID NO:3). FIG. 2B shows the amino acid sequence of chimpanzee PKR2 (SEQ ID NO:4).

FIG. 3 shows a comparison of PKR2 amino acid sequences from squirrel monkey (SEQ ID NO:2), human (SEQ ID NO:7), *M. Fascicularis* (SEQ ID NO:8) and chimpanzee (SEQ ID NO:4).

FIG. 4A shows the nucleotide sequence of rhesus monkey PK2 (SEQ ID NO:5). FIG. 4B shows the amino acid sequence of rhesus monkey PK2 (SEQ ID NO:6).

FIG. 5 shows a comparison of PK2 amino acid sequences from rhesus monkey (SEQ ID NO:6), human (SEQ ID NO:9), and mouse (SEQ ID NO:10).

FIG. 6 shows amino acid sequences of human PK1 (SEQ ID NO:11); mouse PK1 (SEQ ID NO:12); toad BV8 (SEQ ID NO:13); frog BV8 (SEQ ID NO:14); snake MIT1 (SEQ ID NO:15); human PK1-PK2 chimera (SEQ ID NO:16); and human PK2-PK1 chimera (SEQ ID NO:17).

FIG. 8 is a comparison of functional activity of recombinant chimpanzee prokineticin 2 receptor (PKR2)(SEQ ID NO:4) and human PKR2 (SEQ ID NO:7) expressed in Chinese human ovary (CHO) cells.

FIG. 9 depicts the nucleotide sequence of rhesus monkey PK1 (SEQ ID NO:29).

FIG. 10 shows the predicted amino acid sequence of rhesus monkey PK1 (SEQ ID NO:30).

FIG. 11 shows the alignment of rhesus monkey PK1 (SEQ ID NO:30), human PK1 (SEQ ID NO:11) and a human PK1 isoform (SEQ ID NO:31).

FIG. 12 depicts the nucleotide sequence of rhesus monkey PKR1 (SEQ ID NO:34).

FIG. 13 shows the predicted amino acid sequence of rhesus monkey PKR1 (SEQ ID NO:35).

FIG. 14 is an alignment of human PKR1 (SEQ ID NO:36) and rhesus monkey PKR1 (SEQ ID NO:35).

FIG. 15 shows a comparison of functional activity of rhesus monkey PKR1 (SEQ ID NO:35) and human PKR1 (SEQ ID NO:36).

DETAILED DESCRIPTION OF THE INVENTION

Figure 7:
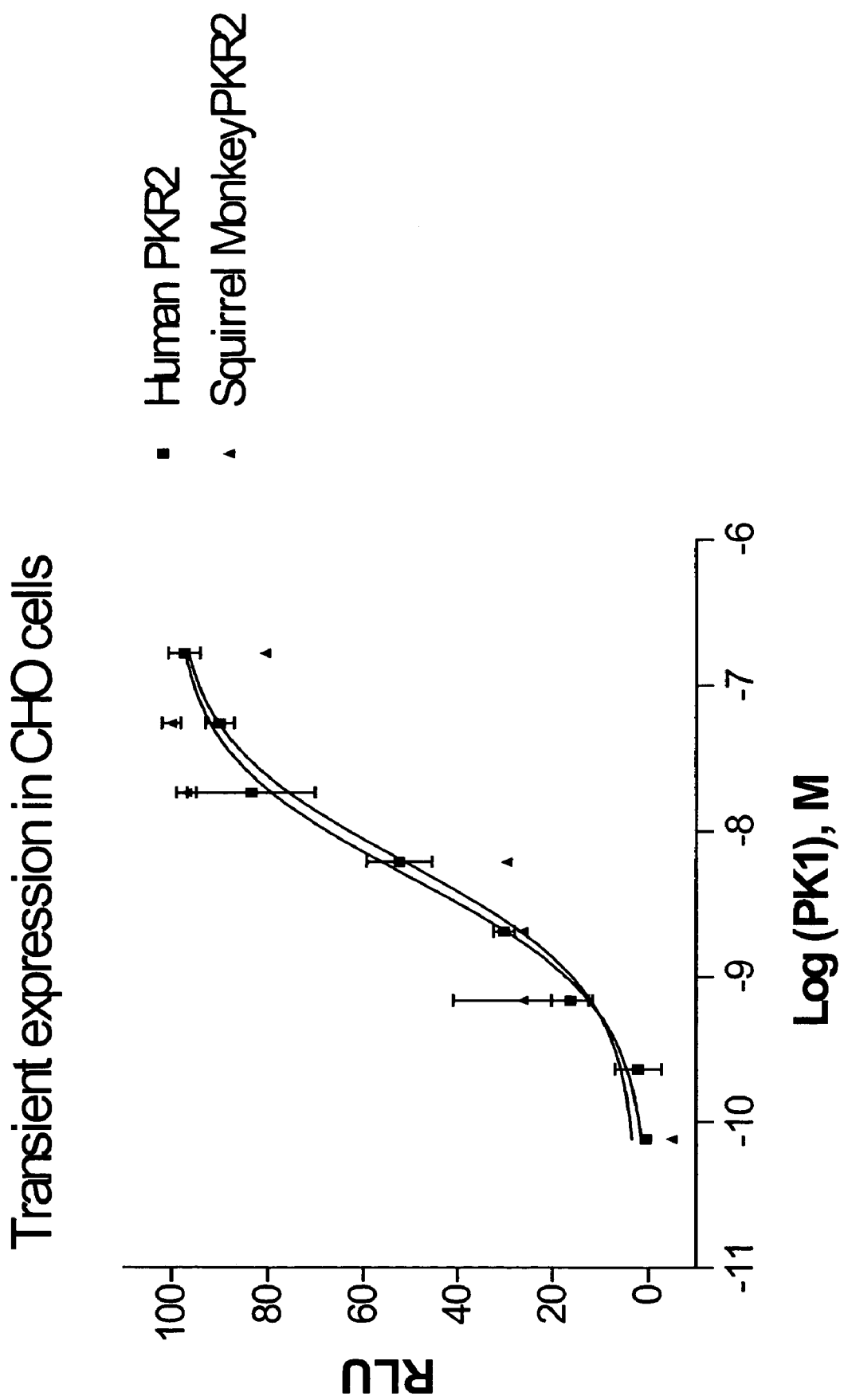
FIG. 7 shows activation of squirrel monkey PKR2 (SEQ ID NO:2) and human PKR2 (SEQ ID NO:7)in response to PK1, as demonstrated by an increase in calcium mobilization.

The invention provides newly identified primate prokineticin receptor 2 (PKR2) polypeptides and prokineticin 2 (PK2) polypeptides, as well as encoding nucleic acid molecules. In particular, PKR2 polypeptides from squirrel monkey and chimpanzee and PKR2, PK1 and PK2 from rhesus monkey are provided. The PKR2, PK1 and PK2 polypeptides of the invention can be used, for example, in screening methods for identifying prokineticin receptor modulating compounds, including receptor agonists and antagonists.

Agonists and antagonists identified using the methods of the invention can be beneficially used to modulate PKR1 and/or PKR2 activity in an individual to treat a condition associated with aberrant low or high level of PKR1 and/or PKR2 activity. For example, because PKR2s can mediate circadian rhythm function in animals (Cheng et al. *Nature* 247:405-410 (2002)), a PKR2 modulating compound can be used to treat disorders of circadian rhythm function, such as sleep disorders, shift work disorders, seasonal depression and jet lag.

Further, because PKR2s can mediate angiogenesis in a variety of tissues (LeCouter et al., *Nature* 412:877-884 (2001); Lin et al. *J. Biol. Chem.* 277:19 (2002)), including endothelium, a PKR2 antagonist can be used to reduce or inhibit angiogenesis in prokineticin receptor expressing tissues. Such an antagonist can be useful for treating cancer and female reproductive disorders such as menorrhagia, endometriosis, dysfunctional uterine bleeding, fibroids and adenoyosis.

Also, because PKR2s can mediate gastric contractility and motility, as well as mediate secretion of gastric acid and pepsinogen, a PKR2 modulating compound can be used to treat, for example, gastric reflux disorder (GERD) irritable bowel syndrome, postoperative ileus, diabetic gastroparesis, chronic constipation and can be used for reducing gastrointestinal side effects of chemotherapy. Moreover, because PKR2s can mediate neurogenesis, a PKR2 receptor modulating compound can be used to treat neurological disorders, including those induced by stroke and trauma. Other indications that can be treated using a PKR2 modulating compound include ischemic heart disease, critical limb ischemia, wound healing and burns, cancer, diabetic retinopathy, and inflammatory diseases such as arthritis and psoriasis.

In addition, due to the sequence similarity between PKR1 and PKR2, an assay method of the invention can employ a PKR1 as a model of PKR2 binding and vice-versa. Thus, a PKR1 can be employed to identify a likely agonist or antagonist of PKR2.

The rhesus monkey PKR1 amino acid sequence (SEQ ID NO:35) disclosed herein differs from human PKR1 (SEQ ID NO:36) at several positions, as shown in FIG. 14. For example, in comparison to human PKR1 (SEQ ID NO:36), rhesus monkey PKR1 (SEQ ID NO:35) contains an alanine at position 22 rather than a valine, an alanine rather than a threonine at position 31, a glycine rather than a serine at position 40, a valine versus an isoleucine at position 82, an isoleucine versus a valine at position 135, an arginine versus a lysine at position 210, a phenylalanine rather than a valine at position 246, a asparagines versus an aspartic acid at position 348 and an alanine instead of a valine at position 350.

The squirrel monkey PKR2 amino acid sequence (SEQ ID NO:2) disclosed herein differs from known primate PKR2 amino acid sequences at several amino acid positions, as is shown in FIG. 3. For example, in comparison to human PKR2 (SEQ ID NO:7) (GenBank AF506288), the squirrel monkey PKR2 sequence contains an alanine residue rather than a threonine at position 11, a valine residue rather than an isoleucine at position 69, a glutamine residue rather than an arginine at position 248, a methionine residue rather than threonine at position 282, a lysine residue rather than an arginine at position 368, and an alanine residue rather than a threonine at position 374; in comparison to *Cercopithecus aethiops* (vervet monkey) PKR2 (U.S. Patent Application Publication 0030059856), which appears to be identical to *Macaca Fascicularis* (long-tailed macaque) PKR2 (SEQ ID NO:8) (PCT publication WO 01/53308), the squirrel monkey PKR2 amino acid sequence (SEQ ID NO:2) contains a valine residue rather than an isoleucine at position 69, a glutamine residue rather than an arginine at position 248, a methionine residue rather than threonine at position 282, an arginine residue rather than a tryptophan at position 357, an aspartic acid residue rather than a glutamic acid at position 364, and a lysine residue rather than an arginine at position 368. Thus, the disclosed squirrel monkey PKR2 amino acid sequence differs from both human and vervet monkey/macaque PKR2 amino acid sequences at multiple amino acid positions.

The chimpanzee PKR2 amino acid sequence (SEQ ID NO:4) disclosed herein differs from known primate PKR2 amino acid sequences in several amino acid positions, also as is shown in FIG. 3. For example, in comparison to human PKR2 (SEQ ID NO:7) (GenBank AF506288), the chimpanzee PKR2 sequence contains an alanine residue rather than a threonine at position 11, a leucine residue rather than a phenylalanine at position 50, a valine residue rather than an isoleucine at position 56, and an alanine residue rather than a threonine at position 374; in comparison to *Cercopithecus aethiops* (vervet monkey) PKR2 (U.S. Patent Application Publication 0030059856), which appears to be identical to *Macaca Fascicularis* (SEQ ID NO:8) (long-tailed macaque) PKR2 (PCT publication WO 01/53308), the disclosed chimpanzee PKR2 (SEQ ID NO:4) sequence contains a leucine residue rather than a phenylalanine at position 50, a valine residue rather than an isoleucine at position 56, an arginine residue rather than a tryptophan at position 357, and an aspartic acid residue rather than a glutamic acid at position 364. Thus, the disclosed chimpanzee PKR2 amino acid sequence differs from both human and vervet monkey/macaque PKR2 amino acid sequences at multiple amino acid positions.

In an embodiment, the invention provides an isolated squirrel monkey PKR2 polypeptide containing the amino acid sequence referenced as SEQ ID NO:2. As used herein, the term "prokineticin receptor 2" or "PKR2" refers to a heptahelical membrane-spanning polypeptide that binds to a prokineticin and signals through a G-protein coupled signal transduction pathway in response to prokineticin binding. The terms "squirrel monkey prokineticin receptor 2" and "squirrel monkey PKR2" refer to a polypeptide comprising the amino acid sequence of squirrel monkey PKR2 shown in FIG. 1B (SEQ ID NO:2).

In another embodiment, the invention provides an isolated chimpanzee PKR2 polypeptide containing the amino acid sequence referenced as SEQ ID NO:4. The terms "chimpanzee prokineticin receptor 2," "chimpanzee PKR2, "*Pan troglodytes* PKR2," and "*P. troglodytes* PKR2" refer to a polypeptide comprising the amino acid sequence of chimpanzee PKR2 shown in FIG. 2B (SEQ ID NO:4).

In a further embodiment, the invention provides an isolated rhesus monkey PKR1 polypeptide containing the amino acid sequence of SEQ ID NO:35. The terms "rhesus monkey prokineticin receptor 1," "rhesus monkey PKR1," and "rhesus PKR1" all refer to a polypeptide comprising an amino acid sequence of rhesus monkey PKR1 shown in FIG. 13 (SEQ ID NO:35).

In another embodiment, the invention provides an isolated rhesus monkey PK1 polypeptide comprising the amino acid sequence of SEQ ID NO:30. The rhesus monkey PK1 differs from known PK1 amino acid sequences at three amino acid positions, as is shown in FIG. 11. As can be seen in FIG. 11, as compared to human PK1 (SEQ ID NO:11) rhesus monkey PK1 (SEQ ID NO:30) has a leucine rather than an arginine at position 5, a phenylalanine versus a leucine at position 10 and a valine instead of an isoleucine at position 66.

In yet another embodiment, the invention provides an isolated rhesus monkey PK2 polypeptide containing the amino acid sequence referenced as SEQ ID NO:6. The rhesus monkey PK2 amino acid sequence disclosed herein differs from known PK2 amino acid sequences at several amino acid positions, as is shown in FIG. 5. For example, in comparison to human PK2 (see GenBank NM 021935 and Sheppard et al. U.S. Pat. No. 6,485,938), the rhesus monkey PK2 sequence contains a valine residue rather than a phenylalanine at position 51, and an arginine residue rather than a glutamine at position 79; in comparison to mouse/rat PK2 (GenBank AF 487280), the disclosed rhesus monkey PK2 sequence contains a lysine residue rather than a glutamine at position 36, a leucine residue rather than a valine at position 37, and a valine residue rather than a tryptophan at position 51. Thus, the disclosed rhesus monkey PK2 amino acid sequence differs from both human and mouse/rat PK2 at multiple amino acid positions.

As used herein, the term "prokineticin" or "PK" refers to a peptide that binds to a prokineticin receptor and elicits signaling by the receptor through a G-protein coupled signal transduction pathway. The term "rhesus monkey PK2 polypeptide" refers to a polypeptide comprising the amino acid sequence of rhesus prokineticin 2 shown as the non-underlined sequence in FIG. 4B (SEQ ID NO:6) and to a fragment of the reference polypeptide that has prokineticin activity. The term "rhesus monkey PK1 polypeptide" refers to a polypeptide comprising the amino acid sequence of rhesus monkey prokineticin 1 of SEQ ID NO:30 and to a fragment of the reference polypeptide that has prokineticin activity. Because of the homology between PKR2 and PKR1, which have amino acid sequences that are about 85% identical, a PK2 polypeptide of the invention can function as a PKR2 or PKR1 agonist. Likewise, a PK1 polypeptide of the invention can function as a PKR2 or a PKR1 agonist. Thus, a PK2 polypeptide of the invention can be used as a PKR2 agonist in the screening methods of the invention as well as in a variety of applications in which PKR1 or PKR2 activation is desired. In the same manner, a PK1 polypeptide of the invention can be used as a PKR1 agonist in the screening methods of the invention, as well as in a variety of applications in which PKR1 or PKR2 activation is desired.

A polypeptide of the invention can contain a reference amino acid sequence, such as SEQ ID NO:2, 4 or 6, 30 or 35 together with a heterologous amino acid sequence. Examples of heterologous amino acid sequences include purification tags, detection tags, and cell localization tags. Non-limiting examples of polypeptide tags that can be contained in a polypeptide of the invention include GST tags, His tags, Flag tags, Myc tags, hemagglutinin tags, multiple affinity purification (MAFT), and tandem affinity purification (TAP) tags.

The invention provides an isolated nucleic acid molecule comprising a sequence that encodes squirrel monkey PKR2 amino acid sequence SEQ ID NO:2. The squirrel monkey PKR2 nucleic acid molecule of the invention can have nucleotide sequence SEQ ID NO:1, or substantially the same nucleotide sequence as SEQ ID NO:1, or a fragment thereof, and optionally can contain a heterologous sequence, such as a tag. Further provided is an isolated nucleic acid molecule comprising a sequence that encodes chimpanzee PKR2 amino acid sequence SEQ ID NO:4. The chimpanzee PKR2 nucleic acid molecule of the invention can have nucleotide sequence SEQ ID NO:3, or substantially the same nucleotide sequence as SEQ ID NO:3, or a fragment thereof, and optionally can contain a heterologous sequence, such as a tag.

The invention also provides an isolated nucleic acid molecule comprising a sequence that encodes rhesus monkey PK2 amino acid sequence SEQ ID NO:6. The rhesus monkey PK2 nucleic acid molecule of the invention can have nucleotide sequence SEQ ID NO:5, or substantially the same nucleotide sequence as SEQ ID NO:5, or a fragment thereof, and optionally can contain a heterologous sequence, such as a tag.

The invention further provides an isolated nucleic acid molecule comprising a sequence that encodes rhesus monkey PKR1 amino acid sequence SEQ ID NO:35. The rhesus monkey PKR1 nucleic acid molecule of the invention can have nucleotide sequence SEQ ID NO:34, or substantially the same nucleotide sequence as SEQ ID NO:34, or a fragment thereof, and optionally can contain a heterologous sequence, such as a tag.

A nucleic acid molecule of the invention can be linked to a variety of heterologous nucleotide sequences, which can encode a heterologous polypeptide or peptide if desired. Exemplary heterologous nucleotide sequences include, a restriction site, a promoter or other regulatory element, a detection tag, an a nucleotide sequence that encodes a tag or other useful sequence in the polypeptide. Non-limiting examples of such tags include a purification tag useful in the isolation of the encoded polypeptide and a detection tag useful in the detection of the encoded polypeptide.

As used herein, the term "nucleic acid molecule" refers to a polynucleotide, including an oligonucleotide, of natural or synthetic origin, which can be single- or double-stranded, can correspond to genomic DNA, cDNA or RNA, and can represent either the sense or antisense strand or both.

The term "nucleic acid molecule" is intended to include nucleic acid molecules that contain one or more non-natural nucleotides, such as nucleotides having modifications to the base, the sugar, or the phosphate portion, or having one or more non-natural linkages, such as phosphorothioate linkages. Such modifications can be advantageous in increasing the stability of the nucleic acid molecule, particularly when used in hybridization applications.

Furthermore, the term "nucleic acid molecule" is intended to include nucleic acid molecules modified to contain a detectable moiety, such as a radiolabel, a fluorochrome, a ferromagnetic substance, a luminescent tag or a detectable binding agent such as biotin. Nucleic acid molecules containing such moieties are useful as probes for detecting the presence or expression of a PKR2 nucleic acid molecule.

A nucleic acid of the invention is considered substantially the same as a subject nucleic acid if it encodes a polypeptide that is at least 80% (e.g. at least 85%, 90%, 95%, 98% or 99%) identical to the polypeptide encoded by the subject nucleic acid. A nucleotide is substantially the same as a subject nucleotide if its sequence encodes a polypeptide which has up to Na amino acid alterations over the entire length of the polypeptide encoded by the subject nucleotide, wherein Na is the maximum number of amino acid alterations, and is calculated by the formula $$Na = Xa - (Xa\ Y),$$

in which Xa is the total number of amino acids in SEQ ID NO:35, and Y has a value of 0.80 (corresponding to 80% identity), 0.85 (85% identity), 0.90 (90% identity), 0.95 (95% identity), 0.98 (98% identity) or 0.99 (99% identity), wherein any non-integer product of Xa and Y is rounded down to the nearest integer prior to subtracting such product from Xa.

As used herein, the term "isolated nucleic acid molecule" is intended to mean that the nucleic acid molecule is altered, by the hand of man, from how it is found in its natural environment. For example, an isolated nucleic acid molecule can be a molecule operatively linked to an exogenous nucleic acid sequence. An isolated nucleic acid molecule can also be a molecule removed from some or all of its normal flanking nucleic acid sequences.

The invention provides vectors that contain a nucleic acid molecule of the invention, and isolated host cells containing the vector. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. The vectors of the invention will generally contain elements such as an origin of replication compatible with the intended host cells; transcription termination and RNA processing signals; one or more selectable markers compatible with the intended host cells; and one or more multiple cloning sites. Optionally, the vector can further contain heterologous sequences encoding tag sequences, such as GST tags, and/or a protease cleavage site, such as a Factor Xa site, which facilitate expression and purification of the encoded polypeptide.

The choice of particular elements to include in a vector will depend on factors such as the intended host cells; the insert size; whether expression of the inserted sequence is desired; the desired copy number of the vector; the desired selection system, and the like. The factors involved in ensuring compatibility between a host cell and a vector for different applications are well known in the art.

In applications in which the vectors are to be used for recombinant expression of the encoded polypeptide, the isolated nucleic acid molecules will generally be operatively linked to a promoter of gene expression, which may be present in the vector or in the inserted nucleic acid molecule. An isolated nucleic acid molecule encoding a squirrel monkey PKR2 of the invention, a chimpanzee PKR2 of the invention, a rhesus monkey PKR1, a rhesus monkey PK1 or a rhesus monkey PK2 of the invention can be operatively linked to a promoter of gene expression. As used herein, the term "operatively linked" means that the nucleic acid molecule is positioned with respect to either the endogenous promoter, or a heterologous promoter, in such a manner that the promoter will direct the transcription of RNA using the nucleic acid molecule as a template.

Methods for operatively linking a nucleic acid to a heterologous promoter are well known in the art and include, for example, cloning the nucleic acid into a vector containing the desired promoter, or appending the promoter to a nucleic acid sequence using PCR. A nucleic acid molecule operatively linked to a promoter of RNA transcription can be used to express prokineticin transcripts and polypeptides in a desired host cell or in vitro transcription-translation system.

The choice of promoter to operatively link to an invention nucleic acid molecule will depend on the intended application, and can be determined by those skilled in the art. For example, if a particular gene product may be detrimental to a particular host cell, it may be desirable to link the invention nucleic acid molecule to a regulated promoter, such that gene expression can be turned on or off. Alternatively, it may be desirable to have expression driven by either a weak or strong constitutive promoter. Exemplary promoters suitable for mammalian cell systems include, for example, the SV40 early promoter, the cytomegalovirus (CMV) promoter, the mouse mammary tumor virus (MMTV) steroid-inducible promoter, and the Moloney murine leukemia virus (MMLV) promoter. Exemplary promoters suitable for bacterial cell systems include, for example, T7, T3, SP6, lac and trp promoters. An exemplary vector suitable for fusion protein expression in bacterial cells is the pGEX-3X vector (Amersham Pharmacia Biotech, Piscataway, N.J.).

The invention provides cells containing an isolated nucleic acid molecule encoding a polypeptide of the invention, such as a squirrel monkey PKR2 polypeptide containing SEQ ID NO:2 or fragment thereof, a chimpanzee PKR2 polypeptide containing SEQ ID NO:4 or fragment thereof, a rhesus monkey PK2 polypeptide containing SEQ ID NO:6 or fragment thereof, a rhesus monkey PKR1 polypeptide of SEQ ID NO:35 or fragment thereof or a rhesus monkey PK1 polypeptide of SEQ ID NO:30 or a fragment thereof. The isolated nucleic acid molecule contained in the cells will generally be present within a vector, and can be maintained episomally, or incorporated into the host cell genome.

The cells of the invention can be used, for example, for molecular biology applications such as expansion, subcloning or modification of the isolated nucleic acid molecule. For such applications, bacterial cells, such as laboratory strains of *E. coli*, are useful, and expression of the encoded polypeptide is not required.

The cells of the invention can also advantageously be used to recombinantly express and isolate the encoded polypeptide. For such applications bacterial cells (for example, *E. coli*), insect cells (for example, *Drosophila* and *Spodoptera fugiperda*), yeast cells (for example, *S. cerevisiae*, *S. pombe*, or *Pichia pastoris*), and vertebrate cells (for example, mammalian primary cells and established cell lines, such as CHO, 293 and COS cells; and amphibian cells, such as *Xenopus* embryos and oocytes).

The invention also provides methods for preparing an isolated polypeptide corresponding to a squirrel monkey PKR2 polypeptide, chimpanzee PKR2 polypeptide, a rhesus monkey PK2 polypeptide, a rhesus monkey PK1 polypeptide and a rhesus monkey PKR1 polypeptide by culturing host cells so as to express a recombinant polypeptide. A variety of well-known methods can be used to introduce a vector into a host cell for expression of a recombinant polypeptide (see, for example, Sambrook et al., *Molecular Cloning: A Laboratory Manual*, Cold Spring Harbor Laboratory, New York (1992) and Ansubel et al., *Current Protocols in Molecular Biology*, John Wiley and Sons, Baltimore, Md. (1998)). The selected method will depend, for example, on the selected host cells.

An isolated polypeptide of the invention can be prepared by biochemical procedures, and can be isolated from host cells that recombinantly express the polypeptide, or from tissues or cells that normally express the polypeptides. A variety of well-known biochemical procedures routinely used in the art, including membrane fractionation, chromatography, electrophoresis and ligand affinity methods, and immunoaffinity methods with the prokineticin antibodies described herein, can be used. An isolated polypeptide of the invention can also be prepared by chemical synthesis procedures known in the art. Following chemical synthesis, an inactive prokineticin can be refolded by the methods described herein to restore activity.

If desired, such as to optimize their functional activity, selectivity, stability or bioavailability, chemically synthesized polypeptides can be modified to include D-stereoisomers, non-naturally occurring amino acids, and amino acid analogs and mimetics. Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983). For certain applications, it can also be useful to incorporate one or more detectably labeled amino acids into a chemically synthesized polypeptide or peptide, such as radiolabeled or fluorescently labeled amino acids.

Methods of recombinantly expressing prokineticins are also known in the art (see US 20020115610A1, US 20030113867A1 and Masuda et al., supra (2001)for examples of bacterial expression and WO 01/36465 and WO 00/52022 for examples of eukaryotic expression). Such methods can involve initially expressing the PK as a fusion protein, such as a fusion with a glutathione-S-transferase tag, Fc tag, 6×His tag, myc epitope, or other tag sequences known in the art. Methods of substantially purifying recombinantly expressed prokineticins, and for removing optional tag sequences, are also known in the art. For example, published patent applications US 20020115610A1 and US 20030113867A1 (each of which is incorporated by reference herein in its entirety) describe conditions for refolding and purifying recombinantly expressed prokineticins that minimize protein aggregation, and also describes methods of confirming correct disulfide bond formation.

In one method for preparing an isolated prokineticin polypeptide, a prokineticin polypeptide may be recombinantly expressed in bacteria as a fusion protein (e.g. as a GST fusion) containing a tag (e.g. a 6×His tag), and partially purified by affinity isolation (e.g. on a nickel column). The fused polypeptide may then be cleaved so as to remove the heterologous protein (e.g. using protease factor Xa cleavage between GST and prokineticin), and the prokineticin polypeptide refolded under conditions described above to minimize protein aggregation. To obtain more highly purified polypeptide, the polypeptide can further be purified by column chromatography (e.g. reverse-phase HPLC). Those skilled in the art will recognize that modification to these preferred methods for recombinantly expressing, refolding and purifying active prokineticin polypeptides can readily be determined, such as employing alternative heterologous sequences, cleavable sequences, tags, host cells and buffer conditions.

Recombinant expression of polypeptides containing multiple cysteine residues can result in the incorrect formation of inter- and intra-molecular disulfide bonds, which can lead to the production of inactive, aggregated bacterial proteins. As disclosed herein, these problems can be overcome using conditions that minimize protein aggregation during refolding of the expressed polypeptide. Exemplary conditions that minimize protein aggregation include one or more of the following refolding conditions: 1) keeping protein concentration low (e.g. about 100 µg/ml); 2) dialysing, rather than diluting, the peptides to remove denaturing agent; 3) omitting oxidants from buffers; 4) maintaining high concentrations of urea in all buffers; 5) maintaining high concentrations of glycerol (e.g. at least about 10%) in buffers; and 6) keeping peptides and buffers at low temperature (e.g. about 4° C.). Of these conditions, it is contemplated that low protein concentration (i.e. less than about 250 µg/ml, preferably less than 200 µg/ml, 150 µg/ml, 100 µg/ml, or 50 µg/ml) and high urea concentration (e.g. at least about 1.5M, such as about 2M, 4M, 6M, 8M or higher) are the most important factors in successful refolding of active prokineticins.

The compositions of the invention can also include crude or partially purified lysates or extracts of cells containing PKR2, PKR1, PK1 or PK2, or combinations thereof, and reconstituted signaling systems containing PKR2, PKR1, PK1 or PK2, or combinations thereof. Artificial signaling systems include, for example, natural or artificial lipid bilayers, such as a liposome or micelle, which promote an active conformation of PKR1 or PKR2. The compositions can further contain cellular fractions or isolated components necessary for producing and detecting a desired predetermined signal.

A composition of the invention further can contain both PKR2 receptor and either or both PK1 and PK2, or another PKR2 receptor agonist, such as a PK2/PK1 chimera or a PK1/PK2 chimera. Alternatively, a composition of the invention further can contain both a PKR1 receptor and either or both PK1 and PK2, or another PKR1 receptor agonist, such as a PK2/PK1 chimera or a PK1/PK2 chimera.

As used herein, the term "isolated" indicates that the polypeptide is altered by the hand of man from how it is found in its natural environment. An "isolated" polypeptide of the invention can be a "substantially purified" molecule, that is at least 60%, 70%, 80%, 90 or 95% free from cellular components with which it is naturally associated. An isolated polypeptide can be in any form, such as in a buffered solution, a suspension, a lyophilized powder, recombinantly expressed in a heterologous cell, bound to a receptor or attached to a solid support.

The squirrel monkey and chimpanzee PKR2 polypeptides of the invention can be used in a variety of screening assays for identifying an antagonist or agonist of a PKR2. In one embodiment, the invention provides a method of identifying a PKR2 agonist. The method involves (a) contacting a PKR2 containing an amino acid sequence referenced as SEQ ID NO:2 or SEQ ID NO:4 with one or more candidate compounds, and (b) identifying a compound that selectively promotes production of a PKR2 signal, the compound being characterized as an agonist of said PKR2.

The rhesus monkey PKR1 polypeptides of the invention can be used in a variety of screening assays for identifying an antagonist or agonist of a PKR1 or PKR2. In one embodiment, the invention provides a method of identifying a PKR1 agonist. The method involves (a) contacting a PKR1 containing an amino acid sequence referenced as SEQ ID NO:35 with one or more candidate compounds, and (b) identifying a compound that selectively promotes production of a PKR1 signal. A compound that selectively promotes PKR1 signal is thus characterized as an agonist of said PKR1.

In another embodiment, the invention provides a method of identifying a PKR2 antagonist. The method involves (a) contacting a PKR2 polypeptide comprising an amino acid sequence referenced as SEQ ID NO:2 or SEQ ID NO:4, with one or more candidate compounds in the presence of a prokineticin, and (b) identifying a compound that selectively inhibits production of a PKR2 signal, said compound being characterized as an antagonist of said PKR2.

In yet another embodiment, the invention provides a method of identifying a PKR1 antagonist. The method involves (a) contacting a PKR1 polypeptide comprising an amino acid sequence referenced as SEQ ID NO:35, with one or more candidate compounds in the presence of a prokineticin, and (b) identifying a compound that selectively inhibits production of a PKR1 signal, said compound being characterized as an antagonist of said PKR1.

As used herein, the terms "prokineticin receptor 2 antagonist" and "PKR2 antagonist" mean a compound that selectively inhibits or decreases normal signal transduction through a prokineticin receptor 2 (PKR2), which can be, for example, a squirrel monkey or chimpanzee PKR2 polypeptide of the invention. A PKR2 antagonist can act by any antagonistic mechanism, such as by binding a PKR2 or PK, thereby inhibiting binding between PK and PKR2. A PKR2 antagonist can also inhibit binding between a specific or non-specific PKR2 agonist and PKR2. Such a specific or non-specific PKR2 agonist can be, for example, a drug that produces unwanted side effects by promoting signaling through the PKR2. A PKR2 antagonist can also act, for example, by inhibiting the binding activity of PK or signaling activity of PKR2. For example, a PKR2 antagonist can act by altering the state of phosphorylation or glycosylation of PKR2. A PKR2 antagonist can also be an inverse agonist, which decreases PKR2 signaling from a baseline amount of constitutive PKR2 signaling activity.

As used herein, the terms "prokineticin receptor 1 antagonist" and "PKR1 antagonist" mean a compound that selectively inhibits or decreases normal signal transduction through a prokineticin receptor 1 (PKR1), which can be, for example, a rhesus monkey PKR1 polypeptide of the invention. A PKR1 antagonist can act by any antagonistic mechanism, such as by binding a PKR1 or PK, thereby inhibiting binding between PK and PKR1. A PKR1 antagonist can also inhibit binding between a specific or non-specific PKR1 agonist and PKR1. Such a specific or non-specific PKR1 agonist can be, for example, a drug that produces unwanted side effects by promoting signaling through the PKR1. A PKR1 antagonist can also act, for example, by inhibiting the binding activity of PK or signaling activity of PKR1. For example, a PKR1 antagonist can act by altering the state of phosphorylation or glycosylation of PKR1. A PKR1 antagonist can also be an inverse agonist, which decreases PKR1 signaling from a baseline amount of constitutive PKR1 signaling activity.

As used herein, the terms "prokineticin receptor 2 agonist" and "PKR2 agonist" mean a compound that selectively promotes or enhances normal signal transduction through a prokineticin receptor 2 (PKR2), which can be, for example, a squirrel monkey or chimpanzee PKR2 polypeptide of the invention. A PKR2 agonist can act by any agonistic mechanism, such as by binding a prokineticin receptor at the normal prokineticin (PK) binding site, thereby promoting PKR2 signaling. A PKR2 agonist can also act, for example, by potentiating the binding activity of PK or signaling activity of PKR2. An agonist of a PKR2 also can function as an agonist of a PKR1 because PK1 and PK2 both can bind to PKR1 and PKR2. As such, a PKR1 agonist can be tested for its ability to function as a PKR2 agonist using the screening methods described herein; and a PKR2 agonist can be tested for its ability to function as a PKR1 agonist using the screening methods described herein.

As used herein, the terms "prokineticin receptor 1 agonist" and "PKR1 agonist" mean a compound that selectively promotes or enhances normal signal transduction through a prokineticin receptor 1 (PKR1), which can be, for example, a rhesus monkey PKR1. An agonist of PKR1 can act by any agonistic mechanism, such as by binding a prokineticin receptor at the normal prokineticin (PK) binding site, thereby promoting PKR1 signaling. A PKR1 agonist can also act, for example, by potentiating the binding activity of PK or signaling activity of PK12. An agonist of a PKR1 also can function as an agonist of a PKR1 because PK1 and PK2 both can bind to PKR1 and PKR2. As such, a PKR2 agonist can be tested for its ability to function as a PKR1 agonist using the screening methods described herein; and a PKR1 agonist can be tested for its ability to function as a PKR2 agonist using the screening methods described herein.

Specific examples of PKR2 agonists include the rhesus monkey, human, and mouse PK2 amino acid sequences shown in FIG. 5, as well as the human and mouse PK1 amino acid sequences (SEQ ID NOS:11 and 12, respectively), toad Bv8 amino acid sequence (SEQ ID NO:13), frog Bv8 amino acid sequence (SEQ ID NO:14), snake MIT1 amino acid sequence (SEQ ID NO:15), chimeric PK1-PK2 amino acid sequences (SEQ ID NOS:16 and 17), as shown in FIG. 6, and rhesus monkey PK1 amino acid sequence shown in FIG. 10 (SEQ ID NO:30).

Specific examples of PKR1 agonists include the rhesus monkey, human, and mouse PK2 amino acid sequences shown in FIG. 5, as well as the human and mouse PK1 amino acid sequences (SEQ ID NOS:11 and 12, respectively), toad Bv8 amino acid sequence (SEQ ID NO:13), frog Bv8 amino acid sequence (SEQ ID NO:14), snake MIT1 amino acid sequence (SEQ ID NO:15), chimeric PK1-PK2 amino acid sequences (SEQ ID NOS:16 and 17), as shown in FIG. 6, and rhesus monkey PK1 amino acid sequence shown in FIG. 10 (SEQ ID NO:30).

A screening assay used in a method of the invention for identifying a PKR1 or PKR2 agonist or antagonist can involve detecting a signal produced by a PKR1 or PKR2. As used herein, the term "receptor signal" is intended to mean a readout, detectable by any analytical means, that is a qualitative or quantitative indication of activation of G-protein-dependent signal transduction through PKR2. Assays used to determine such qualitative or quantitative activation of G-protein-dependent signal transduction through PKR1 or PKR2, are referred to below as "signaling assays."

A signaling assay can be performed to determine whether a candidate compound is a PKR1 or PRR2 agonist or antagonist. In such an assay, a PKR1 or PKR2 receptor, such as the squirrel monkey or chimpanzee PKR2 polypeptides or the rhesus monkey PKR1 disclosed herein, is contacted with one or more candidate compounds under conditions wherein the PKR1 or PKR2 produces a signal in response to an agonist, such as PK1 or PK2. In response to PKR1 or PKR2 activation, a signal can increase or a decrease from an unstimulated PKR1 or PKR2 baseline signal. A signal can be an increasing signal, for example, when the amount of detected second messenger molecule is increased in response to PKR1 or PKR2 activation. A signal can be a decreasing signal, for example, when the detected second messenger molecule is destroyed, for example, by hydrolysis, in response to PKR1 or PKR2 activation.

Similarly, a signaling assay can be performed to determine whether a candidate compound is a PKR1 or PKR2 antagonist. In such a signaling assay, a PKR1 or PKR2 is contacted with one or more candidate compounds under conditions wherein the PKR1 or PKR2 produces a signal in response to an agonist, such as PK1 or PK2, and a compound is identified that reduces production of the signal.

Signaling through G proteins can lead to increased or decreased production or liberation of second messengers, including, for example, arachidonic acid, acetylcholine, diacylglycerol, cGMP, cAMP, inositol phosphate, such as inositol-1,4,5-trisphosphate, and ions, including $Ca^{++}$ ions; altered cell membrane potential; GTP hydrolysis; influx or efflux of amino acids; increased or decreased phosphorylation of intracellular proteins; or activation of transcription.

Various assays, including high throughput automated screening assays, to identify alterations in G-protein coupled signal transduction pathways are well known in the art. Various screening assay that measure $Ca^{++}$, cAMP, voltage changes and gene expression are reviewed, for example, in Gonzalez et al., *Curr. Opin. in Biotech.* 9:624-631 (1998); Jayawickreme et al., *Curr. Opin. Biotech.* 8:629-634 (1997); and Coward et al., *Anal. Biochem.* 270:2424-248 (1999). Yeast cell-based bioassays for high-throughput screening of drug targets for G-protein coupled receptors are described, for example, in Pausch, *Trends in Biotech.* 15:487-494 (1997). A variety of cell-based expression systems, including bacterial, yeast, baculovirus/insect systems and mammalian cells, useful for detecting G-protein coupled receptor agonists and antagonists are reviewed, for example, in Tate et al., *Trends in Biotech.* 14:426-430 (1996).

Assays to detect and measure G-protein-coupled signal transduction can involve first contacting a sample containing a PKR1 or PKR2 polypeptide of the invention, such as an isolated cell, membrane or artificial membrane, such as a liposome or micelle, with a detectable indicator. A detectable indicator can be any molecule that exhibits a detectable difference in a physical or chemical property in the presence of the substance being measured, such as a color change. Calcium indicators, pH indicators, and metal ion indicators, and assays for using these indicators to detect and measure selected signal transduction pathways are described, for example, in Haugland, *Molecular Probes Handbook of Fluorescent Probes and Research Chemicals*, Sets 20-23 and 25 (1992-94). For example, calcium indicators and their use are well known in the art, and include compounds like Fluo-3 AM, Fura-2, Indo-1, FURA RED, CALCIUM GREEN, CALCIUM ORANGE, CALCIUM CRIMSON, BTC, OREGON GREEN BAPTA, which are available from Molecular Probes, Inc., Eugene Oreg., and described, for example, in U.S. Pat. Nos. 5,453,517, 5,501,980 and 4,849, 362. Exemplary methods for performing signaling assays for PKR2 activity are known in the art (see, for example, US 20020115610A1, which describes mobilization assays.)

If desired, a receptor signal other than $Ca^{2+}$ influx can be used as the readout for PKR1 or PKR2 activation. The specificity of a G-protein for cell-surface receptors is determined by the C-terminal five amino acids of the Gα subunit. The nucleotide sequences and signal transduction pathways of different classes and subclasses of Gα subunits in a variety of eukaryotic and prokaryotic organisms are well known in the art. Thus, any convenient G-protein mediated signal transduction pathway can be assayed by preparing a chimeric Gα containing the C-terminal residues of a Gα that couples to a PKR1 or PKR2 of the invention, such as Gαq, with the remainder of the protein corresponding to a Gα that couples to the signal transduction pathway it is desired to assay.

An assay to identify compounds that function as PKR1 or PKR2 agonists or antagonists are generally performed under conditions in which contacting the receptor with a known receptor agonist would produce a receptor signal. If desired, the assay can be performed in the presence of a known PKR1 or PKR2 agonist, such as a PK1 or PK2. The agonist concentration can be within 10-fold of the $EC_{50}$. Thus, an agonist that competes with PK2, PK1 or a PK2/PK1 chimera, for signaling through the PKR1 or PKR2, or indirectly potentiates the signaling activity of PK1 or PK2, can be readily identified. Similarly, an agonist that competes with PK2, PK1 or a PK2/PK1 chimera for signaling through the PKR1 or PKR2 can be readily identified.

Likewise, an antagonist that prevents PK2, PK1 or a PK2/PK1 chimera from binding the PKR1 or PKR2, or indirectly decreases the signaling activity of PKR1 or PKR2, also can be identified. Similarly, an antagonist that prevents PK2, PK1 or a PK2/PK1 chimera from binding the PKR1, or indirectly decreases the signaling activity of PKR1, also can be identified. The candidate compound can be tested at a range of concentrations to establish the concentration where half-maximal signaling occurs; such a concentration is generally similar to the dissociation constant (Kd) for PKR1 or PKR2 binding.

A binding assay can be performed to identify compounds that are PKR1 or PKR2 agonists or antagonists. In such an assay, a PKR1 or PKR2 polypeptide of the invention can be contacted one or more candidate compounds under conditions in which an agonist such as PK2 binds to the PKR1 or PKR2 and a compound that binds to PKR1 or PKR2 or that reduces binding of the agonist to PKR1 or PKR2 can be identified. Contemplated binding assays can involve detectably labeling a candidate compound, or competing an unlabeled candidate compound with a detectably labeled PK agonist, such as a PK2, PK1 or PK2/PK1 chimera. A detectable label can be, for example, a radioisotope, fluorochrome, ferromagnetic substance, or luminescent substance. Exemplary radiolabels useful for labeling compounds include $^{125}I$, $^{14}C$ and $^3H$. Methods of detectably labeling organic molecules, either by incorporating labeled amino acids into the compound during synthesis, or by derivatizing the compound after synthesis, are known in the art.

In order to determine whether a candidate compound decreases binding of detectably labeled PK, the amount of binding of a given amount of the detectably labeled PK is determined in the absence of the candidate compound. Generally the amount of detectably labeled PK will be less than its $K_d$, for example, 1/10 of its $K_d$. Under the same conditions, the amount of binding of the detectably labeled PK2, PK1 or PK2/PK1 chimera in the presence of the candidate compound is determined. A decrease in binding due to a candidate compound characterized as a PKR1 or PKR2 ligand is evidenced by at least 2-fold less, such as at least 10-fold to at least 100-fold less, such as at least 1000-fold less, binding of detectably labeled PK2, PK1 or PK2/PK1 chimera to PKR1 or PKR2 in the presence of the candidate compound than in the absence of the candidate compound. An exemplary assay for determining binding of detectably labeled PK2, PK1 or PK2/PK1 chimera to PKR1 or PKR2 is the radioligand filter binding assay described in Li et al. *Molecular Pharmacology* 59:692-698 (2001)).

Either low- and high-throughput assays suitable for detecting selective binding interactions between a receptor and a ligand include, for example, fluorescence correlation spectroscopy (FCS) and scintillation proximity assays (SPA) reviewed in Major, *J. Receptor and Signal Transduction Res.* 15:595-607 (1995); and in Sterrer et al., *J. Receptor and Signal Transduction Res.* 17:511-520 (1997)). Binding assays can be performed in any suitable assay format including, for example, cell preparations such as whole cells or membranes that contain a PKR1 or PKR2 of the invention, or substantially purified PKR1 or PKR2 of the invention, either in solution or bound to a solid support.

As used herein, the term "candidate compound" refers to any biological or chemical compound. For example, a candidate compound can be a naturally occurring macromolecule, such as a polypeptide, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it will be appreciated that the larger the number of candidate compounds, the greater the likelihood of identifying a compound having the desired activity in a screening assay. Additionally, large numbers of compounds can be processed in high-throughput automated screening assays.

Assay methods for identifying compounds that selectively bind to or modulate signaling through a PKR1 or PKR2 generally involve comparison to a control. One type of a "control" is a preparation that is treated identically to the test preparation, except the control is not exposed to the candidate compound. Another type of "control" is a preparation that is similar to the test preparation, except that the control preparation does not express the receptor, or has been modified so as not to respond selectively to PK2 or PK1. In this situation, the response of the test preparation to a candidate compound is compared to the response (or lack of response) of the control preparation to the same compound under substantially the same reaction conditions.

A compound identified to be an agonist or antagonist of a PKR1 or PKR2 polypeptide of the invention can be tested for its ability to modulate one or more effects on the function of a cell or animal. For example, a PKR1 or PKR2 agonist or antagonist can be tested for an ability to modulate circadian rhythm function, angiogenesis, gastrointestinal contraction and motility and secretion of gastric acid or pepsinogen, neurological conditions and pain.

Exemplary assays for determining for determining the effect of a compound on circadian rhythm function are described, for example, in Cheng et al. *Nature* 247:405-410 (2002). Exemplary assays for determining the effect of a compound on angiogenesis are described, for example, in U.S. Pat. No. 5,753,230 and PCT publication WO 97/15666 and U.S. Pat. No. 5,639,725, which describe tumor model systems; Langer et al., *Science* 193:707-72 (1976); O'Reilly, et al., *Cell* 79:315-328 (1994); and U.S. Pat. No. 5,753,230. Exemplary assays for determining the effect of a compound on GI contraction and motility are described, for example, in Li et al. *Mol Pharmacol.* 59(4):692-8 (2001), and Thomas et al., *Biochem. Pharmacol.* 51:779-788 (1993).

Exemplary assays for determining for determining the effect of a compound on gastric acid or pepsinogen secretion are described, for example, in Soll, *Am. J. Physiol* 238: G366-G375 (1980); Sol and Walsh, *Annu. Rev. Physiol.* 41:35-53(1979); Lavezzo et al., *Int J Tissue React* 6(2):155-165 (1984)) and in isolated gastric mucosae (Rangachari, *Am. J. Physiol.* 236:E733-E737 (1979), Bunce et al. *Br. J. Pharmacol* 58:149-156 (1976); and Lavezzo et al., *Int J Tissue React* 6(2):155-165 (1984)); Howden et al., *Aliment Pharmacol Ther* 1(4):305-315 (1987); Hirschowitz et al. *J. Pharmacol Exp Ther* 224(2):341-5 (1983), and Wilson et al. *Gig Dis Sci* 29(9):797-801 (1984).

Exemplary assays for determining the effect of a compound on neurological conditions include animal models of trauma due to stroke or neural injury are known in the art.

One experimental model of stroke involves occluding the right middle cerebral artery and both common carotid arteries of rats for a short period, followed by reperfusion (Moore et al., *J. Neurochem.* 80:111-118). An experimental model of CNS injury is the fluid percussion injury (FPI) model, in which moderate impact (1.5-2.0 atm) is applied to the parietal cerebral cortex (Akasu et al., *Neurosci. Lett.* 329: 305-308 (2002). Experimental models of spinal cord injury are also used in the art (Scheifer et al., *Neurosci. Lett.* 323:117-120 (2002). Suitable models for neural damage due to oxidative stress, hypoxia, radiation and toxins are also known in the art.

Exemplary assays for determining the effect of a compound on pain include well-known animal models of pain, such as the Mouse Writhing Assay, the Tail Flick Assay, the Sciatic Nerve Ligation assay, the Formalin Test and the Dorsal Root Ganglia Ligation assay (see, for example, Bennett and Xie, *Pain* 33:87-107 (1988); and Lee et al., *Neurosci. Lett.* 186:111-114 (1995); Dewey et al., *J. Pharm. Pharmacol.* 21:548-550 (1969); Koster et al., *Fed. Proc.* 18:412 (1959);pain (Malmberg and Yaksh, *The Journal of Pharmacology and Experimental Therapeutics* 263:136-146 (1992)).

The rhesus monkey prokineticin polypeptide of the invention, as well as a compound identified using a method of the invention, can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in ex vivo and in vivo assays referenced herein.

The methods of the invention can involve administering a PRK1 or PKR2 agonist or antagonist to prevent or treat a variety of conditions as described herein above. As used herein, the term "administering" when used in reference to a PRK1 or PKR2 agonist or antagonist means providing to or contacting a cell, tissue or animal with the PRK1 or PKR2 antagonist. The term encompasses administering a PRK1 or PKR2 agonist or antagonist in vitro or ex vivo, as to a cell or tissue, which can be a cell or tissue removed from an animal or a cell or tissue placed in or adapted to culture; as well as in vivo, as to an animal. The total amount of a compound can be administered as a single dose or by infusion over a relatively short period of time, or can be administered in multiple doses administered over a more prolonged period of time. Additionally, the compound can be administered in a slow-release matrix, which can be implanted for systemic delivery at or near the site of the target tissue. Contemplated matrices useful for controlled release of compounds, including therapeutic compounds, are well known in the art, and include materials such as Depo-Foam™, biopolymers, micropumps, and the like.

A compound can be administered to a mammal by a variety of routes known in the art including, for example, intracerebrally, intraspinally, intravenously, intramuscularly, subcutaneously, intraorbitally, intracapsularly, intraperitoneally, intracisternally, intra-articularly, orally, intravaginally, rectally, topically, intranasally, or transdermally.

Generally, a compound, such as a prokineticin polypeptide and other compounds identified using a method of the invention, are administered to an animal as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or detrains; antioxidants, such as ascorbic acid or glutathione; chelating agents; and low molecular weight proteins (see for example, "Remington's Pharmaceutical Sciences" 18th ed., Mack Publishing Co. (1990)).

For applications that require the compounds to cross the blood-brain barrier, or to cross cell membranes, formulations that increase the lipophilicity of the compound can be useful. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. Other approaches for formulating a compound such that it crosses the blood-brain barrier are known in the art and include the use of nanoparticles, which are solid colloidal particles ranging in size from 1 to 1000 nm (Lockman et al., *Drug Dev. Ind. Pharm.* 28:1-13 (2002)), and peptides and peptidomimetics that serve as transport vectors (Pardridge, *Nat. Rev. Drug Discov.* 1:131-139 (2002).

The invention provides an antibody selective for squirrel monkey PKR2 polypeptide SEQ ID NO:2 that does not substantially bind to another primate or non-primate PKR2. In addition, the invention provides an antibody selective for chimpanzee PKR2 polypeptide SEQ ID NO:4 that does not substantially bind to another primate or non-primate PKR2. Also provided is an antibody selective for rhesus monkey PK2 SEQ ID NO:6 that does not substantially bind to another primate or non-primate PK2. Further provided is an antibody selective for rhesus monkey PK1 SEQ ID NO:30 that does not substantially bind to another primate or non-primate PK1. Also provided is an antibody selective for rhesus monkey PKR1 SEQ ID NO:35 that does not substantially bind to another primate or non-primate PKR1. The antibodies of the invention can be used, for example, to detect expression of a squirrel monkey PKR2 or rhesus monkey PK2 in research and diagnostic applications. The term "antibody," as used herein, is intended to include molecules having selective binding activity for an amino acid sequence corresponding to a reference polypeptide of at least about $1 \times 10^5$ M$^{-1}$, preferably at least $1 \times 10^7$ M$^{-1}$, more preferably at least $1 \times 10^9$ M$^{-1}$. The term "antibody" includes both polyclonal and monoclonal antibodies, as well as antigen binding fragments of such antibodies (e.g. Fab, F(ab')$_2$, Fd and Fv fragments and the like). In addition, the term "antibody" is intended to encompass non-naturally occurring antibodies, including, for example, single chain antibodies, chimeric antibodies, bifunctional antibodies, CDR-grafted antibodies and humanized antibodies, as well as antigen-binding fragments thereof.

Methods of preparing and isolating antibodies, including polyclonal and monoclonal antibodies, using peptide and polypeptide immunogens, are well known in the art and are described, for example, in Harlow and Lane, *Antibodies: A Laboratory Manual*, Cold Spring Harbor Laboratory Press (1988). Non-naturally occurring antibodies can be con-

EXAMPLE I

Cloning of Rhesus Monkey PK2

This example describes cloning of a rhesus monkey prokineticin 2 cDNA.

PCR methods were used to obtain a full-length rhesus monkey PK2 cDNA from reverse-transcribed RNA isolated from rhesus monkey testis. The rhesus monkey PK2 cDNA was amplified with Pfu polymerase using the following primers for PCR: GGCGCCATGAGGAGCCTGTGCTGC (SEQ ID NO:37) and ATTATTCTGATACAGAATTTT (SEQ ID NO:18) followed by nested PCR using the following primers:

```
GGCGCCATGAGGAGCCTGTGCTGC        (SEQ ID NO:19) and

CTCTTCAAGTGACATTTTCTA.          (SEQ ID NO:20)
```

The Pfu-catalyzed PCR amplification was carried out for 30 cycles with each cycle consisting of 94° C. denaturing for 30 seconds, 55° annealing for 45 seconds, 68° C. elongation for 90 seconds. The PCR product was cloned into PCRII vector (INVITROGEN CORPORATION, Carlsbad, Calif.) and confirmed by DNA sequencing.

EXAMPLE II

Cloning of Squirrel Monkey PKR2

This example describes cloning of a squirrel monkey prokineticin receptor 2 cDNA.

PCR methods were used to obtain a full-length squirrel monkey PKR2 cDNA from reverse-transcribed RNA isolated from squirrel monkey brain. The squirrel monkey PKR2 cDNA was amplified with Pfu polymerase using the following oligonucleotide primers:

```
ATCACCATGGCAGCCCAGAATGGAAACACCAG    (SEQ ID NO:21)

and TCACTTCAGCCTGATACAGTCCAC.       (SEQ ID NO:22)
```

The Pfu-catalyzed PCR amplification was carried out for 50 cycles with each cycle consisting of 94° C. denaturing for 30 seconds, 58° C. annealing for 45 seconds, 68° C. elongation for 90 seconds. The PCR product was cloned into PCRII vector (INVITROGEN CORPORATION, Carlsbad, Calif.) and confirmed by DNA sequencing. For calcium mobilization assays described herein below, the squirrel monkey PKR2 was cloned into pcDNA3.1Zeo (INVITROGEN CORPORATION, Carlsbad, Calif.).

EXAMPLE III

Cloning of Chimpanzee PKR2

This example describes cloning of a chimpanzee prokineticin receptor 2 cDNA (SEQ ID NO:3).

PCR methods were used to obtain a full-length chimpanzee (*Pan troglodytes*) PKR2 cDNA from reverse-transcribed RNA isolated from chimpanzee salivary gland tissues. The chimpanzee PKR2 cDNA was amplified with Pfu polymerase using the following primers:

```
                                              (SEQ ID NO:23)
ATCACCATGGCAGCCCAGAATGGAAACACCAG, (SEQ ID NO:24)
ATXGCCATTGACAGATATCTXGCCATXGTTCACCCC  (X: T or C), (SEQ ID NO:25)
AGATATCTGTCAATGGCXATGGCCAGCAAGGCATTG  (X: A or G),
and (SEQ ID NO:26)
TCACTTCAGCCTGATACAGTCCAC.
```

The Pfu-catalyzed PCR amplification was carried out for 45 cycles with each cycle consisting of 94° C. denaturing for 30 seconds, 58° C. annealing for 45 seconds, 68° C. elongation for 90 seconds. The PCR products of primer 1 and 2 (product 1) and those of primer 3 and 4 (product 2) were cloned into PCRII vector (INVITROGEN CORPORATION, Carlsbad, Calif.) and confirmed by DNA sequencing. The complete chimpanzee PKR2 sequence was generated by ligation of product 1 and product 2 with a conserved Eco RV site.

EXAMPLE IV

Squirrel Monkey PKR2 Activity is Comparable to Human PKR2 Activity

This example provides evidence that squirrel monkey PKR2 is activated in response to PK1 and has activity comparable to that of human PKR2.

The activity of squirrel monkey PKR2 was assessed by measuring calcium mobilization in response to PK1. For the calcium mobilization assays, squirrel monkey PKR2 cDNA (SEQ ID NO:1) was transiently transfected into CHO cells stably expressing photoprotein aequorin using lipofectamine (INVITROGEN CORPORATION, Carlsbad, Calif.). After 48 hours, the transfected cells were charged in Opti-MEM (INVITROGEN CORPORATION, Carlsbad, Calif.) containing 8 µM of coelenterazine cp at 37° C. for 2 hours. Cells were then detached by brief typsinization and maintained in Hank's Balanced Salt Solution (HBSS) plus 10 mM HEPES (pH 7.5) and 0.1% BSA at about $5 \times 10^5$ cells/ml. 100 µl of cells were injected into the tubes with 20 µl recombinant human PK1 diluted in HBSS plus 10 mM HEPES (pH 7.5) and 0.1% BSA. Luminescence measurements were made using a MONOLIGHT 2010 luminometer (Analytical Luminescence Laboratory, San Diego, Calif.).

Results of these experiments are shown in FIG. 7, which reveals that squirrel monkey PKR2 (SEQ ID NO:2) has activity comparable to human PKR2 (SEQ ID NO:7) with an EC50 on the order of 10 nM.

EXAMPLE V

Molecular Cloning and Characterization of Non-human Primate Prokineticin and Prokineticin Receptors The activity of the chimpanzee PKR2 (SEQ ID NO:4) was assessed by measuring calcium mobilization in response to rHuPK2 (SEQ ID NO:7). For the calcium mobilization assays, chimpanzee PKR2 cDNA (SEQ ID NO:3) was transiently transfected into CHO cells stably expressing photoprotein aequorin using lipofectamine (Invitrogen Corporation, Carlsbad, Calif.). After 48 hours, the transfected cells were charged in Opti-MEM (Invitrogen Corporation, Carlsbad, Calif.) containing 8 µM of coelenterazine cp at 37° C. for 2 hours. Cells were then detached by brief typsinization and maintained in Hank's Balanced Salt Solution (HBSS) plus 10 mM HEPES (pH 7.5) and 0.1% BSA at about $5 \times 10^5$ cells/ml. 100 µl of cells were injected into the tubes with 20 µl recombinant human PK2 (SEQ ID NO:7) diluted in HBSS plus 10 mM HEPES (pH 7.5) and 0.1% BSA. Luminescence measurements were made using a MONOLIGHT 2010 luminometer (Analytical Luminescence Laboratory, San Diego, Calif.).

Results of these experiments are shown in FIG. 8, which shows that the chimpanzee PKR2 (SEQ ID NO:3) has activity comparable to the human PKR2 (SEQ ID NO:7) with an EC50 of approximately 10 nM.

Cloning of rhesus monkey PK1 (SEQ ID NO:30). PCR methodology was used to obtain a full-length rhesus monkey PK1 cDNA from reverse-transcribed RNA isolated from rhesus monkey testis (Oregon Primate Center). The rhesus monkey PK1 cDNA (SEQ ID NO:29) was amplified with Pfu polymerase using the following primers for PCR:

```
GAGAGGCATCTAAGCAGGCAGTGT      (SEQ ID NO:27) and

CAATGCACCCAAGAGCCTGTGCCCA     (SEQ ID NO:28)
```

The Pfu-catalyzed PCR amplification was carried out for 30 cycles with each cycle consisting of 94° C. denaturing for 30 seconds, 55° annealing for 45 seconds, 68° C. elongation for 90 seconds. The PCR product was cloned into PCRII vector (Invitrogen Corporation, Carlsbad, Calif.) and confirmed by DNA sequencing. The nucleotide (SEQ ID NO: 29) and amino acid (SEQ ID NO:30) sequences for rhesus monkey PK1 are shown in FIGS. 9 and 10.

A comparison of the alignment of rhesus monkey PK1 (SEQ ID NO:30) with human PK1 (SEQ ID NO:11) and a human isoform of PK1 (SEQ ID NO:31) reported by Takeda scientists is shown in FIG. 11. This alignment reveals a) three substitutions between rhesus monkey PK1 (SEQ ID NO:30) and human PK1 (SEQ ID NO:11) and b) two substitutions between rhesus monkey PK1 (SEQ ID NO:30) and the human PK1 isoform (SEQ ID NO:31).

EXAMPLE VI

Cloning of Rhesus Monkey PKR1 and Expression in CHO Cells

PCR methodology was used to obtain a full-length rhesus monkey PKR1 cDNA (SEQ ID NO:34) from reverse-transcribed RNA isolated from rhesus monkey testis (Oregon Primate Center). The rhesus monkey PKR1 cDNA (SEQ ID NO:35) was amplified with Pfu polymerase using the following oligonucleotide primers:

```
CAGATGGAGACCACCATGGGGTTCATG;    (SEQ ID NO:32) and

TTATTTTAGTCTGATGCAGTCCACCTCTTC  (SEQ ID NO:33)
```

The Pfu-catalyzed PCR amplification was carried out for 50 cycles with each cycle consisting of 94° C. denaturing for 30 seconds, 58° C. annealing for 45 seconds, 68° C. elongation for 90 seconds. The PCR product was cloned into PCRII vector (Invitrogen Corporation, Carlsbad, Calif.) and confirmed by DNA sequencing. For calcium mobilization assays described herein below, the rhesus monkey PKR1 was cloned into pcDNA3.1Zeo (Invitrogen Corporation, Carlsbad, Calif.). The rhesus monkey PKR1 nucleic acid (SEQ ID NO:34) is 1182 nucleotides in length. The nucleotide (SEQ ID NO:34) and predicted amino acid (SEQ ID NO:35) sequences for rhesus monkey PKR1 are shown in FIGS. 12 and 13, respectively.

The alignment of the amino acid sequences for human PKR1 (SEQ ID NO:36) and rhesus monkey PKR1 (SEQ ID NO:35) is shown in FIG. 14. This alignment reveals that there are nine amino acid residues different between human and rhesus monkey PKR1. Essentially all of these are conservative changes.

The rhesus monkey PKR1 (SEQ ID NO:35) was expressed in CHO cells and shown to have activity comparable to that of the rHuPKR1 (SEQ ID NO:36). The activity of the rhesus monkey PKR1 (SEQ ID NO:35) was assessed by measuring calcium mobilization in response to PK2. For the calcium mobilization assays, rhesus monkey PKR1 cDNA (SEQ ID NO:34) was transiently transfected into CHO cells stably expressing photoprotein aequorin using lipofectamine (Invitrogen Corporation, Carlsbad, Calif.). After 48 hours, the transfected cells were charged in Opti-MEM (Invitrogen Corporation, Carlsbad, Calif.) containing 8 µM of coelenterazine cp at 37° C. for 2 hours. Cells were then detached by brief typsinization and maintained in Hank's Balanced Salt Solution (HBSS) plus 10 mM HEPES (pH 7.5) and 0.1% BSA at about $5 \times 10^5$ cells/ml. 100 µl of cells were injected into the tubes with 20 µl recombinant human PK2 diluted in HBSS plus 10 mM HEPES (pH 7.5) and 0.1% BSA. Luminescence measurements were made using a Monolight 2010 luminometer (Analytical Luminescence Laboratory, San Diego, Calif.).

Results obtained from these experiments are shown in FIG. 15, which shows that the rhesus monkey PKR1 (SEQ ID NO:35) has activity comparable to the human PKR1 (SEQ ID NO:36) with an EC50 value of approximately 10 nM.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. An isolated squirrel monkey prokineticin receptor 2 (PKR2) polypeptide, comprising the amino acid sequence of SEQ ID NO:2.

2. An isolated chimpanzee prokineticin receptor 2 (PKR2) polypeptide, comprising the amino acid sequence of SEQ ID NO:4.

* * * * *

SEQUENCE LISTING

<160> NUMBER OF SEQ ID NOS: 37

<210> SEQ ID NO 1
<211> LENGTH: 1155
<212> TYPE: DNA
<213> ORGANISM: Saimiri sciureus
<220> FEATURE:
<221> NAME/KEY: CDS
<222> LOCATION: (1)...(1155)

<400> SEQUENCE: 1

| | | | | | | | | | | | | | | | | |
|---|---|---|---|---|---|---|---|---|---|---|---|---|---|---|---|---|
| atg | gca | gcc | cag | aat | gga | aac | acc | agt | ttt | gca | ccc | aac | ttt | aat | cca | 48 |
| Met | Ala | Ala | Gln | Asn | Gly | Asn | Thr | Ser | Phe | Ala | Pro | Asn | Phe | Asn | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | caa | gac | cat | gcc | tcc | tcc | ctc | tcc | ttc | aac | ttc | agt | tat | ggt | gat | 96 |
| Pro | Gln | Asp | His | Ala | Ser | Ser | Leu | Ser | Phe | Asn | Phe | Ser | Tyr | Gly | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | gac | ctc | cct | atg | gat | gag | gat | gag | gac | atg | acc | aag | acc | cgg | acc | 144 |
| Tyr | Asp | Leu | Pro | Met | Asp | Glu | Asp | Glu | Asp | Met | Thr | Lys | Thr | Arg | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| ttc | ttt | gca | gcc | aag | att | gtc | atc | ggc | att | gca | ctg | gca | ggc | atc | atg | 192 |
| Phe | Phe | Ala | Ala | Lys | Ile | Val | Ile | Gly | Ile | Ala | Leu | Ala | Gly | Ile | Met | |
| | 50 | | | | | 55 | | | | | 60 | | | | | |

| | | | | | | | | | | | | | | | | |
|---|---|---|---|---|---|---|---|---|---|---|---|---|---|---|---|---|
| ctg | gtc | tgt | ggt | gtc | ggt | aac | ttt | gtc | ttt | atc | gct | gcc | ctc | acc | cgc | 240 |
| Leu | Val | Cys | Gly | Val | Gly | Asn | Phe | Val | Phe | Ile | Ala | Ala | Leu | Thr | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tat | aag | aag | ctg | cgc | aac | ctc | acc | aat | ctg | ctc | att | gcc | aac | ctg | gcc | 288 |
| Tyr | Lys | Lys | Leu | Arg | Asn | Leu | Thr | Asn | Leu | Leu | Ile | Ala | Asn | Leu | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | tcc | gac | ttc | ctg | gtg | gcc | atc | atc | tgc | tgc | ccc | ttt | gag | atg | gac | 336 |
| Ile | Ser | Asp | Phe | Leu | Val | Ala | Ile | Ile | Cys | Cys | Pro | Phe | Glu | Met | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| tac | tat | gtg | gtc | cgg | cag | ctc | tcc | tgg | gag | cat | ggc | cac | gtg | ctc | tgt | 384 |
| Tyr | Tyr | Val | Val | Arg | Gln | Leu | Ser | Trp | Glu | His | Gly | His | Val | Leu | Cys | |
| | | 115 | | | | | 120 | | | | | 125 | | | | |

| | | | | | | | | | | | | | | | | |
|---|---|---|---|---|---|---|---|---|---|---|---|---|---|---|---|---|
| gcc | tct | gtc | aac | tac | ctg | cgc | acc | gtc | tcc | ctc | tac | gtc | tcc | acc | aat | 432 |
| Ala | Ser | Val | Asn | Tyr | Leu | Arg | Thr | Val | Ser | Leu | Tyr | Val | Ser | Thr | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| gcc | ttg | ctg | gcc | atc | gcc | att | gac | aga | tat | ctc | gcc | att | gtt | cac | ccc | 480 |
| Ala | Leu | Leu | Ala | Ile | Ala | Ile | Asp | Arg | Tyr | Leu | Ala | Ile | Val | His | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttg | aaa | cca | agg | atg | aat | tat | caa | acg | gcc | tcc | ttc | ctg | atc | gcc | ttg | 528 |
| Leu | Lys | Pro | Arg | Met | Asn | Tyr | Gln | Thr | Ala | Ser | Phe | Leu | Ile | Ala | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gtc | tgg | atg | gta | tcc | att | ctc | att | gcc | atc | cca | tca | gcc | tac | ttt | gca | 576 |
| Val | Trp | Met | Val | Ser | Ile | Leu | Ile | Ala | Ile | Pro | Ser | Ala | Tyr | Phe | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| aca | gaa | acc | gtc | ctc | ttt | att | gtc | aag | agc | cag | gag | aag | atc | ttc | tgt | 624 |
| Thr | Glu | Thr | Val | Leu | Phe | Ile | Val | Lys | Ser | Gln | Glu | Lys | Ile | Phe | Cys | |
| | | 195 | | | | | 200 | | | | | 205 | | | | |

| | | | | | | | | | | | | | | | | |
|---|---|---|---|---|---|---|---|---|---|---|---|---|---|---|---|---|
| ggc | cag | atc | tgg | ccc | gtg | gat | cag | cag | ctc | tac | tac | aag | tcc | tac | ttc | 672 |
| Gly | Gln | Ile | Trp | Pro | Val | Asp | Gln | Gln | Leu | Tyr | Tyr | Lys | Ser | Tyr | Phe | |
| | 210 | | | | | 215 | | | | | 220 | | | | | |

| | | | | | | | | | | | | | | | | |
|---|---|---|---|---|---|---|---|---|---|---|---|---|---|---|---|---|
| ctc | ttc | atc | ttt | ggt | gtg | gag | ttc | gtg | ggt | cct | gtg | gtc | acc | atg | acc | 720 |
| Leu | Phe | Ile | Phe | Gly | Val | Glu | Phe | Val | Gly | Pro | Val | Val | Thr | Met | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctg | tgc | tac | gcc | agg | att | tcc | cag | gag | ctc | tgg | ttc | aag | gca | gtc | cct | 768 |
| Leu | Cys | Tyr | Ala | Arg | Ile | Ser | Gln | Glu | Leu | Trp | Phe | Lys | Ala | Val | Pro | |
| | | | | 245 | | | | | 250 | | | | | 255 | | |

```
                                                                              -continued ggg ttc cag aca gag cag atc cgt aag cgg ctg cgc tgc cgc agg aag        816
Gly Phe Gln Thr Glu Gln Ile Arg Lys Arg Leu Arg Cys Arg Arg Lys
        260                 265                 270 aca gtc ctg gtg ctc atg tgc atc ctc atg gcc tac gtg cta tgc tgg        864
Thr Val Leu Val Leu Met Cys Ile Leu Met Ala Tyr Val Leu Cys Trp
            275                 280                 285 gca ccc ttc tat ggt ttc acc atc gta cgc gac ttc ttc ccc acc gtg        912
Ala Pro Phe Tyr Gly Phe Thr Ile Val Arg Asp Phe Phe Pro Thr Val
290                 295                 300 ttc gta aag gaa aag cac tac ctc act gcc ttc tac gtg gtc gag tgc        960
Phe Val Lys Glu Lys His Tyr Leu Thr Ala Phe Tyr Val Val Glu Cys
305                 310                 315                 320 atc gcc atg agc aac agc atg atc aac acc gtg tgc ttc gtg acg gtc       1008
Ile Ala Met Ser Asn Ser Met Ile Asn Thr Val Cys Phe Val Thr Val
                325                 330                 335 aag aac aac acc atg aag tat ttc aag aag atg atg ctg ctg cac tgg       1056
Lys Asn Asn Thr Met Lys Tyr Phe Lys Lys Met Met Leu Leu His Trp
            340                 345                 350 cgt ccc tcc cag cgg ggg agc aag tcc agt gcc gac ctt gac ctt aag       1104
Arg Pro Ser Gln Arg Gly Ser Lys Ser Ser Ala Asp Leu Asp Leu Lys
        355                 360                 365 acg aac ggg gtg cct gcc acg gaa gag gtg gac tgt atc agg ctg aag       1152
Thr Asn Gly Val Pro Ala Thr Glu Glu Val Asp Cys Ile Arg Leu Lys
    370                 375                 380 tga                                                                    1155
 *

<210> SEQ ID NO 2
<211> LENGTH: 384
<212> TYPE: PRT
<213> ORGANISM: Saimiri sciareus

<400> SEQUENCE: 2

Met Ala Ala Gln Asn Gly Asn Thr Ser Phe Ala Pro Asn Phe Asn Pro
 1               5                  10                  15

Pro Gln Asp His Ala Ser Ser Leu Ser Phe Asn Phe Ser Tyr Gly Asp
                20                  25                  30

Tyr Asp Leu Pro Met Asp Glu Asp Glu Asp Met Thr Lys Thr Arg Thr
            35                  40                  45

Phe Phe Ala Ala Lys Ile Val Ile Gly Ile Ala Leu Ala Gly Ile Met
        50                  55                  60

Leu Val Cys Gly Val Gly Asn Phe Val Phe Ile Ala Ala Leu Thr Arg
 65                  70                  75                  80

Tyr Lys Lys Leu Arg Asn Leu Thr Asn Leu Leu Ile Ala Asn Leu Ala
                 85                  90                  95

Ile Ser Asp Phe Leu Val Ala Ile Ile Cys Cys Pro Phe Glu Met Asp
            100                 105                 110

Tyr Tyr Val Val Arg Gln Leu Ser Trp Glu His Gly His Val Leu Cys
        115                 120                 125

Ala Ser Val Asn Tyr Leu Arg Thr Val Ser Leu Tyr Val Ser Thr Asn
130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
            180                 185                 190
```

```
Thr Glu Thr Val Leu Phe Ile Val Lys Ser Gln Glu Lys Ile Phe Cys
        195                 200                 205
Gly Gln Ile Trp Pro Val Asp Gln Leu Tyr Tyr Lys Ser Tyr Phe
    210                 215                 220
Leu Phe Ile Phe Gly Val Glu Phe Val Gly Pro Val Val Thr Met Thr
225                 230                 235                 240
Leu Cys Tyr Ala Arg Ile Ser Gln Glu Leu Trp Phe Lys Ala Val Pro
                245                 250                 255
Gly Phe Gln Thr Glu Gln Ile Arg Lys Arg Leu Arg Cys Arg Arg Lys
            260                 265                 270
Thr Val Leu Val Leu Met Cys Ile Leu Met Ala Tyr Val Leu Cys Trp
        275                 280                 285
Ala Pro Phe Tyr Gly Phe Thr Ile Val Arg Asp Phe Phe Pro Thr Val
    290                 295                 300
Phe Val Lys Glu Lys His Tyr Leu Thr Ala Phe Tyr Val Val Glu Cys
305                 310                 315                 320
Ile Ala Met Ser Asn Ser Met Ile Asn Thr Val Cys Phe Val Thr Val
                325                 330                 335
Lys Asn Asn Thr Met Lys Tyr Phe Lys Lys Met Met Leu Leu His Trp
            340                 345                 350
Arg Pro Ser Gln Arg Gly Ser Lys Ser Ser Ala Asp Leu Asp Leu Lys
        355                 360                 365
Thr Asn Gly Val Pro Ala Thr Glu Glu Val Asp Cys Ile Arg Leu Lys
    370                 375                 380

<210> SEQ ID NO 3
<211> LENGTH: 1155
<212> TYPE: DNA
<213> ORGANISM: Pan troglodyte
<220> FEATURE:
<221> NAME/KEY: CDS
<222> LOCATION: (1)...(1154)

<400> SEQUENCE: 3 atg gca gcc cag aat gga aac acc agt ttc gca ccc aac ttt aat cca       48
Met Ala Ala Gln Asn Gly Asn Thr Ser Phe Ala Pro Asn Phe Asn Pro
 1               5                  10                  15 ccg caa gac cat gcc tcc tcc ctc tcc ttt aac ttc agt tat ggt gat       96
Pro Gln Asp His Ala Ser Ser Leu Ser Phe Asn Phe Ser Tyr Gly Asp
             20                  25                  30 tat gac ctc cct atg gat gag gat gag gac atg acc aag acc cgg acc      144
Tyr Asp Leu Pro Met Asp Glu Asp Glu Asp Met Thr Lys Thr Arg Thr
         35                  40                  45 ttc ctc gca gcc aag atc gtc gtt ggc att gca ctg gca ggc atc atg      192
Phe Leu Ala Ala Lys Ile Val Val Gly Ile Ala Leu Ala Gly Ile Met
     50                  55                  60 ctg gtc tgc ggc atc ggt aac ttt gtc ttt atc gct gcc ctc acc cgc      240
Leu Val Cys Gly Ile Gly Asn Phe Val Phe Ile Ala Ala Leu Thr Arg
 65                  70                  75                  80 tat aag aag ttg cgc aac ctc acc aat ctg ctc att gcc aac ctg gcc      288
Tyr Lys Lys Leu Arg Asn Leu Thr Asn Leu Leu Ile Ala Asn Leu Ala
                 85                  90                  95 atc tcc gac ttc ctg gtg gcc atc atc tgc tgc ccc ttc gag atg gac      336
Ile Ser Asp Phe Leu Val Ala Ile Ile Cys Cys Pro Phe Glu Met Asp
            100                 105                 110 tac tac gtg gta cgg cag ctc tcc tgg gag cat ggc cac gtg ctc tgt      384
Tyr Tyr Val Val Arg Gln Leu Ser Trp Glu His Gly His Val Leu Cys
        115                 120                 125
```

-continued

| | | |
|---|---|---|
| gcc tcc gtc aac tac ctg cgc acc gtc tcc ctc tac gtc tcc acc aat<br>Ala Ser Val Asn Tyr Leu Arg Thr Val Ser Leu Tyr Val Ser Thr Asn<br>130                               135                           140 | 432 | |

```
gcc tcc gtc aac tac ctg cgc acc gtc tcc ctc tac gtc tcc acc aat       432
Ala Ser Val Asn Tyr Leu Arg Thr Val Ser Leu Tyr Val Ser Thr Asn
130                 135                 140 gcc ttg ctg gcc atc gcc att gac aga tat ctc gcc att gtt cac cct       480
Ala Leu Leu Ala Ile Ala Ile Asp Arg Tyr Leu Ala Ile Val His Pro
145                 150                 155                 160 ttg aaa cca cgg atg aat tat caa acg gcc tcc ttc ctg atc gcc ttg       528
Leu Lys Pro Arg Met Asn Tyr Gln Thr Ala Ser Phe Leu Ile Ala Leu
                165                 170                 175 gtc tgg atg gtg tcc att ctc att gcc atc cca tcg gcc tac ttt gca       576
Val Trp Met Val Ser Ile Leu Ile Ala Ile Pro Ser Ala Tyr Phe Ala
            180                 185                 190 aca gaa acc gtc ctc ttt att gtc aag agc cag gag aag atc ttc tgt       624
Thr Glu Thr Val Leu Phe Ile Val Lys Ser Gln Glu Lys Ile Phe Cys
        195                 200                 205 ggc cag atc tgg ccc gtg gat cag cag ctc tac tac aag tcc tac ttc       672
Gly Gln Ile Trp Pro Val Asp Gln Gln Leu Tyr Tyr Lys Ser Tyr Phe
    210                 215                 220 ctc ttc atc ttt ggt gtc gag ttc gtg ggc cct gtg gtc acc atg acc       720
Leu Phe Ile Phe Gly Val Glu Phe Val Gly Pro Val Val Thr Met Thr
225                 230                 235                 240 ctg tgc tat gcc agg atc tcc cgg gag ctc tgg ttc aag gca gtc cct       768
Leu Cys Tyr Ala Arg Ile Ser Arg Glu Leu Trp Phe Lys Ala Val Pro
                245                 250                 255 ggg ttc cag acg gag cag att cgc aag cgg ctg cgc tgc cgc agg aag       816
Gly Phe Gln Thr Glu Gln Ile Arg Lys Arg Leu Arg Cys Arg Arg Lys
            260                 265                 270 acg gtc ctg gtg ctc atg tgc att ctc acg gcc tat gtg ctg tgc tgg       864
Thr Val Leu Val Leu Met Cys Ile Leu Thr Ala Tyr Val Leu Cys Trp
        275                 280                 285 gca ccc ttc tac ggt ttc acc atc gtt cgt gac ttc ttc ccc act gtg       912
Ala Pro Phe Tyr Gly Phe Thr Ile Val Arg Asp Phe Phe Pro Thr Val
    290                 295                 300 ttc gtg aag gaa aag cac tac ctc act gcc ttc tac gtg gtc gag tgc       960
Phe Val Lys Glu Lys His Tyr Leu Thr Ala Phe Tyr Val Val Glu Cys
305                 310                 315                 320 atc gcc atg agc aac agc atg atc aac acc gtg tgc ttc gtg acg gtc      1008
Ile Ala Met Ser Asn Ser Met Ile Asn Thr Val Cys Phe Val Thr Val
                325                 330                 335 aag aac aac acc atg aag tac ttc aag aag atg atg ctg ctg cac tgg      1056
Lys Asn Asn Thr Met Lys Tyr Phe Lys Lys Met Met Leu Leu His Trp
            340                 345                 350 cgt ccc tcc cag cgg ggg agc aag tcc agt gcc gac ctt gac ctc aga      1104
Arg Pro Ser Gln Arg Gly Ser Lys Ser Ser Ala Asp Leu Asp Leu Arg
        355                 360                 365 acc aac ggg gtg ccc gcc aca gaa gag gtg gac tgt atc agg ctg aag      1152
Thr Asn Gly Val Pro Ala Thr Glu Glu Val Asp Cys Ile Arg Leu Lys
    370                 375                 380 tg a                                                                  1155

<210> SEQ ID NO 4
<211> LENGTH: 384
<212> TYPE: PRT
<213> ORGANISM: Pan troglodyte

<400> SEQUENCE: 4

Met Ala Ala Gln Asn Gly Asn Thr Ser Phe Ala Pro Asn Phe Asn Pro
1               5                   10                  15

Pro Gln Asp His Ala Ser Ser Leu Ser Phe Asn Phe Ser Tyr Gly Asp
            20                  25                  30
```

```
Tyr Asp Leu Pro Met Asp Glu Asp Met Thr Lys Thr Arg Thr
     35                  40                  45

Phe Leu Ala Ala Lys Ile Val Val Gly Ile Ala Leu Ala Gly Ile Met
 50                  55                  60

Leu Val Cys Gly Ile Gly Asn Phe Val Phe Ile Ala Ala Leu Thr Arg
65                   70                  75                  80

Tyr Lys Lys Leu Arg Asn Leu Thr Asn Leu Leu Ile Ala Asn Leu Ala
                 85                  90                  95

Ile Ser Asp Phe Leu Val Ala Ile Ile Cys Cys Pro Phe Glu Met Asp
             100                 105                 110

Tyr Tyr Val Val Arg Gln Leu Ser Trp Glu His Gly His Val Leu Cys
             115                 120                 125

Ala Ser Val Asn Tyr Leu Arg Thr Val Ser Leu Tyr Val Ser Thr Asn
     130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                 165                 170                 175

Val Trp Met Val Ser Ile Leu Ile Ala Ile Pro Ser Ala Tyr Phe Ala
             180                 185                 190

Thr Glu Thr Val Leu Phe Ile Val Lys Ser Gln Glu Lys Ile Phe Cys
             195                 200                 205

Gly Gln Ile Trp Pro Val Asp Gln Gln Leu Tyr Tyr Lys Ser Tyr Phe
     210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                 245                 250                 255

Gly Phe Gln Thr Glu Gln Ile Arg Lys Arg Leu Arg Cys Arg Arg Lys
             260                 265                 270

Thr Val Leu Val Leu Met Cys Ile Leu Thr Ala Tyr Val Leu Cys Trp
             275                 280                 285

Ala Pro Phe Tyr Gly Phe Thr Ile Val Arg Asp Phe Phe Pro Thr Val
     290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                 325                 330                 335

Lys Asn Asn Thr Met Lys Tyr Phe Lys Lys Met Met Leu Leu His Trp
             340                 345                 350

Arg Pro Ser Gln Arg Gly Ser Lys Ser Ser Ala Asp Leu Asp Leu Arg
     355                 360                 365

Thr Asn Gly Val Pro Ala Thr Glu Glu Val Asp Cys Ile Arg Leu Lys
     370                 375                 380

<210> SEQ ID NO 5
<211> LENGTH: 1204
<212> TYPE: DNA
<213> ORGANISM: Macaca mulatta
<220> FEATURE:
<221> NAME/KEY: CDS
<222> LOCATION: (5)...(329)

<400> SEQUENCE: 5 cgcc atg agg agc ctg tgc tgc gcc cca ctc ctg ctc ctc ctg ctg ctg      49
```

```
    Met Arg Ser Leu Cys Cys Ala Pro Leu Leu Leu Leu Leu
    1               5                  10                  15 ccg ccg ctg ctg ctc acg ccc cgc gtc ggg gac gcc gcc gtg atc acc         97
Pro Pro Leu Leu Leu Thr Pro Arg Val Gly Asp Ala Ala Val Ile Thr
            20                  25                  30 ggg gct tgt gac aag gac tcc caa tgt ggt gga ggc atg tgc tgt gct         145
Gly Ala Cys Asp Lys Asp Ser Gln Cys Gly Gly Gly Met Cys Cys Ala
            35                  40                  45 gtc agt atc tgg gtt aag agc ata agg att tgc aca cct atg ggc aaa         193
Val Ser Ile Trp Val Lys Ser Ile Arg Ile Cys Thr Pro Met Gly Lys
        50                  55                  60 ctg gga gac agc tgc cat cca ctg act cgt aaa gtt cca ttt gtt ggg         241
Leu Gly Asp Ser Cys His Pro Leu Thr Arg Lys Val Pro Phe Val Gly
    65                  70                  75 cgg agg atg cat cac act tgc cca tgt ctg cca ggc ttg gcc tgt tta         289
Arg Arg Met His His Thr Cys Pro Cys Leu Pro Gly Leu Ala Cys Leu
80                  85                  90                  95 cgg act tca ttt aac cga ttt att tgt tta gcc cga aag t aatcgcttta        339
Arg Thr Ser Phe Asn Arg Phe Ile Cys Leu Ala Arg Lys
                100                 105 aagtagaaac caaatgtgaa tagccacatc ttatctgtaa agtcttactt gtgattgtgc      399
caaacaaaaa atgtgccaga agaaatgct  tttgcttcct caactttcca agtaactttt       459
ttatctttga gttttaaatg attttttttt taatcgggaa ttttactttt ggatagaaat      519
ataaagtgta aggcattgtg gaactggttc tcatttccct gtttgtgttt tggtttggtt      579
tggctttttt cttaaatgtc aaaaacatac ccattttcac aaaaatgagg aaataggaa       639 tttgatattt tgttagagaa acttttttt tcctcaccat cccaagcccc atttgtgccc       699
cgccacacca taccatacat acatacatac atacatacat acatacatac aacttttggt      759
cccttgcctc ttccacctca aagaatttca aggcccttac cttactttat ttttctccat      819
ttctcttccc tgctcttgca ttttaaagtg gtaggtttat ctctttgagt ttgatggcag      879
aatcgctgat gggaatccag cttttttgccg gctatttaaa tagtgaaaag agtttatatg     939
tgaacttgac actccaaact cctctcatgg cgtggacgct gggagtgctg ccggaccctt      999
cctaaacctg tcactcaaga ggacttcggc tctgctgttg ggctggtgtg tggacagaag     1059
gaatggaaag ctaaattaat ttagtccaga tttctaggtt tgggttttc taaaaatgaa      1119 agattacgtt tacttctttt tctttttata agtttttttt ttcttagtct cctacttaga     1179
gatattctag aaaatgtcac ttgaa                                            1204
```

<210> SEQ ID NO 6
<211> LENGTH: 108
<212> TYPE: PRT
<213> ORGANISM: Macaca mulatta

<400> SEQUENCE: 6

```
Met Arg Ser Leu Cys Cys Ala Pro Leu Leu Leu Leu Leu Leu Leu Pro
1               5                   10                  15

Pro Leu Leu Leu Thr Pro Arg Val Gly Asp Ala Ala Val Ile Thr Gly
            20                  25                  30

Ala Cys Asp Lys Asp Ser Gln Cys Gly Gly Gly Met Cys Cys Ala Val
        35                  40                  45

Ser Ile Trp Val Lys Ser Ile Arg Ile Cys Thr Pro Met Gly Lys Leu
    50                  55                  60

Gly Asp Ser Cys His Pro Leu Thr Arg Lys Val Pro Phe Val Gly Arg
65                  70                  75                  80
```

```
Arg Met His His Thr Cys Pro Cys Leu Pro Gly Leu Ala Cys Leu Arg
                85                  90                  95

Thr Ser Phe Asn Arg Phe Ile Cys Leu Ala Arg Lys
            100                 105

<210> SEQ ID NO 7
<211> LENGTH: 384
<212> TYPE: PRT
<213> ORGANISM: Homo sapiens

<400> SEQUENCE: 7

Met Ala Ala Gln Asn Gly Asn Thr Ser Phe Thr Pro Asn Phe Asn Pro
  1               5                  10                  15

Pro Gln Asp His Ala Ser Ser Leu Ser Phe Asn Phe Ser Tyr Gly Asp
                20                  25                  30

Tyr Asp Leu Pro Met Asp Glu Asp Glu Asp Met Thr Lys Thr Arg Thr
                35                  40                  45

Phe Phe Ala Ala Lys Ile Val Ile Gly Ile Ala Leu Ala Gly Ile Met
 50                  55                  60

Leu Val Cys Gly Ile Gly Asn Phe Val Phe Ile Ala Ala Leu Thr Arg
 65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
                100                 105                 110

Tyr Tyr Val Val Arg Gln Leu Ser Trp Glu His Gly His Val Leu Cys
                115                 120                 125

Ala Ser Val Asn Tyr Leu Arg Thr Val Ser Leu Tyr Val Ser Thr Asn
130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
                180                 185                 190

Thr Glu Thr Val Leu Phe Ile Val Lys Ser Gln Glu Lys Ile Phe Cys
                195                 200                 205

Gly Gln Ile Trp Pro Val Asp Gln Gln Leu Tyr Tyr Lys Ser Tyr Phe
                210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
                260                 265                 270

Thr Val Leu Val Leu Met Cys Ile Leu Thr Ala Tyr Val Leu Cys Trp
                275                 280                 285

Ala Pro Phe Tyr Gly Phe Thr Ile Val Arg Asp Phe Phe Pro Thr Val
                290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
```

-continued

```
                340                 345                 350
Arg Pro Ser Gln Arg Gly Ser Lys Ser Ser Ala Asp Leu Asp Leu Arg
            355                 360                 365

Thr Asn Gly Val Pro Thr Thr Glu Glu Val Asp Cys Ile Arg Leu Lys
    370                 375                 380
```

<210> SEQ ID NO 8
<211> LENGTH: 384
<212> TYPE: PRT
<213> ORGANISM: M. fascicularis

<400> SEQUENCE: 8

```
Met Ala Ala Gln Asn Gly Asn Thr Ser Phe Ala Pro Asn Phe Asn Pro
 1               5                  10                  15

Pro Gln Asp His Ala Ser Ser Leu Ser Phe Asn Phe Ser Tyr Gly Asp
            20                  25                  30

Tyr Asp Leu Pro Met Asp Glu Asp Glu Asp Met Thr Lys Thr Arg Thr
        35                  40                  45

Phe Phe Ala Ala Lys Ile Val Ile Gly Ile Ala Leu Ala Gly Ile Met
 50                  55                  60

Leu Val Cys Gly Ile Gly Asn Phe Val Phe Ile Ala Ala Leu Thr Arg
65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
            100                 105                 110

Tyr Tyr Val Val Arg Gln Leu Ser Trp Glu His Gly His Val Leu Cys
        115                 120                 125

Ala Ser Val Asn Tyr Leu Arg Thr Val Ser Leu Tyr Val Ser Thr Asn
    130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
            180                 185                 190

Thr Glu Thr Val Leu Phe Ile Val Lys Ser Gln Glu Lys Ile Phe Cys
        195                 200                 205

Gly Gln Ile Trp Pro Val Asp Gln Gln Leu Tyr Tyr Lys Ser Tyr Phe
    210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
            260                 265                 270

Thr Val Leu Val Leu Met Cys Ile Leu Thr Ala Tyr Val Leu Cys Trp
        275                 280                 285

Ala Pro Phe Tyr Gly Phe Thr Ile Val Arg Asp Phe Phe Pro Thr Val
    290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335
```

```
Lys Asn Thr Met Lys Tyr Phe Lys Met Met Leu Leu His Trp
            340                 345             350

Arg Pro Ser Gln Trp Gly Ser Lys Ser Ser Ala Glu Leu Asp Leu Arg
            355                 360             365

Thr Asn Gly Val Pro Ala Thr Glu Glu Val Asp Cys Ile Arg Leu Lys
        370                 375             380

<210> SEQ ID NO 9
<211> LENGTH: 81
<212> TYPE: PRT
<213> ORGANISM: Homo sapiens

<400> SEQUENCE: 9

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Gln
65                  70                  75                  80

Lys

<210> SEQ ID NO 10
<211> LENGTH: 80
<212> TYPE: PRT
<213> ORGANISM: Mus musculus

<400> SEQUENCE: 10

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Gln Val Gly Asp Ser Cys His Pro Leu Thr Arg Lys Val
        35                  40                  45

Pro Phe Trp Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Arg
65                  70                  75                  80

<210> SEQ ID NO 11
<211> LENGTH: 82
<212> TYPE: PRT
<213> ORGANISM: Homo sapiens

<400> SEQUENCE: 11

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80
```

Leu Lys

<210> SEQ ID NO 12
<211> LENGTH: 86
<212> TYPE: PRT
<213> ORGANISM: Mus musculus

<400> SEQUENCE: 12

Ala Val Ile Thr Gly Ala Cys Glu Arg Asp Ile Gln Cys Gly Ala Gly
1               5                   10                  15

Thr Cys Cys Ala Ile Ser Leu Trp Leu Arg Gly Leu Arg Leu Cys Thr
            20                  25                  30

Pro Leu Gly Arg Glu Gly Glu Glu Cys His Pro Gly Ser His Lys Ile
        35                  40                  45

Pro Phe Leu Arg Lys Arg Gln His His Thr Cys Pro Cys Ser Pro Ser
    50                  55                  60

Leu Leu Cys Ser Arg Phe Pro Asp Gly Arg Tyr Arg Cys Phe Arg Asp
65                  70                  75                  80

Leu Lys Asn Ala Asn Phe
                85

<210> SEQ ID NO 13
<211> LENGTH: 75
<212> TYPE: PRT
<213> ORGANISM: Bufo americanus (toad)

<400> SEQUENCE: 13

Ala Val Ile Thr Gly Ala Cys Asp Lys Asp Val Gln Cys Gly Ser Gly
1               5                   10                  15

Thr Cys Cys Ala Ala Ser Ala Trp Ser Arg Asn Ile Arg Phe Cys Ile
            20                  25                  30

Pro Leu Ser Gly Glu Asp Cys His Pro Ala Ser His Lys Val Pro Tyr
        35                  40                  45

Asp Gly Lys Arg Leu Ser Ser Leu Cys Pro Cys Lys Ser Gly Leu Thr
    50                  55                  60

Cys Ser Lys Ser Gly Glu Lys Phe Lys Cys Ser
65                  70                  75

<210> SEQ ID NO 14
<211> LENGTH: 77
<212> TYPE: PRT
<213> ORGANISM: Anura  Rafinesque (frog)

<400> SEQUENCE: 14

Ala Val Ile Thr Gly Ala Cys Asp Lys Asp Val Gln Cys Gly Ser Gly
1               5                   10                  15

Thr Cys Cys Ala Ala Ser Ala Trp Ser Arg Asn Ile Arg Phe Cys Ile
            20                  25                  30

Pro Leu Gly Asn Ser Gly Glu Asp Cys His Pro Ala Ser His Lys Val
        35                  40                  45

Pro Tyr Asp Gly Lys Arg Leu Ser Ser Leu Cys Pro Cys Lys Ser Gly
    50                  55                  60

Leu Thr Cys Ser Lys Ser Gly Glu Lys Phe Lys Cys Ser
65                  70                  75

<210> SEQ ID NO 15
<211> LENGTH: 80
<212> TYPE: PRT

<213> ORGANISM: Serpentes Linnaeus

<400> SEQUENCE: 15

Ala Val Ile Thr Gly Ala Cys Glu Arg Asp Leu Gln Cys Gly Lys Gly
1               5                   10                  15

Thr Cys Cys Ala Val Ser Leu Trp Ile Lys Ser Val Arg Val Cys Thr
            20                  25                  30

Pro Val Gly Thr Ser Gly Glu Asp Cys His Pro Ala Ser His Lys Ile
        35                  40                  45

Pro Phe Ser Gly Gln Arg Met His His Thr Cys Pro Cys Ala Pro Asn
    50                  55                  60

Leu Ala Cys Val Gln Thr Ser Pro Lys Lys Phe Lys Cys Leu Ser Lys
65                  70                  75                  80

<210> SEQ ID NO 16
<211> LENGTH: 81
<212> TYPE: PRT
<213> ORGANISM: Homo sapiens

<400> SEQUENCE: 16

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

Pro Phe Phe Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Gln
65                  70                  75                  80

Lys

<210> SEQ ID NO 17
<211> LENGTH: 86
<212> TYPE: PRT
<213> ORGANISM: Homo sapiens

<400> SEQUENCE: 17

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
            85

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18

```
attattctga tacagaattt t                                             21

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
ggcgccatga ggagcctgtg ctgc                                          24

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
ctcttcaagt gacattttct a                                             21

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
atcaccatgg cagcccagaa tggaaacacc ag                                 32

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
tcacttcagc ctgatacagt ccac                                          24

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23
atcaccatgg cagcccagaa tggaaacacc ag                                 32

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
atygccattg acagatatct ygccatygtt cacccc                             36

<210> SEQ ID NO 25
<211> LENGTH: 36
<212> TYPE: DNA
```

```
<213> ORGANISM: Artificial Sequence
<220> FEATURE:
<223> OTHER INFORMATION: primer

<400> SEQUENCE: 25
agatatctgt caatggcrat ggccagcaag gcattg                                    36

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
tcacttcagc ctgatacagt ccac                                                 24

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
gagaggcatc taagcaggca gtgt                                                 24

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
caatgcaccc aagagcctgt gccca                                                25

<210> SEQ ID NO 29
<211> LENGTH: 762
<212> TYPE: DNA
<213> ORGANISM: Macaca mulatta
<220> FEATURE:
<221> NAME/KEY: CDS
<222> LOCATION: (14)...(330)

<400> SEQUENCE: 29
ccttcaagtg acc atg aga ggt gcc acg cta gtc tca atc atg ttc ctc            49
            Met Arg Gly Ala Thr Leu Val Ser Ile Met Phe Leu
              1               5                  10 cta gta act gtg tct gac tgt gct gtg atc aca ggg gcc tgt gag cgg           97
Leu Val Thr Val Ser Asp Cys Ala Val Ile Thr Gly Ala Cys Glu Arg
         15                  20                  25 gat gtc cag tgt ggg gca ggc acc tgc tgt gcc atc agc ctg tgg ctt          145
Asp Val Gln Cys Gly Ala Gly Thr Cys Cys Ala Ile Ser Leu Trp Leu
     30                  35                  40 cga ggg ctg cgg atg tgt acc ccg ctg ggg cgg gaa ggc gag gag tgc          193
Arg Gly Leu Arg Met Cys Thr Pro Leu Gly Arg Glu Gly Glu Glu Cys
 45                  50                  55                  60 cat cct ggc agc cac aag gtc ccc ttc ttt agg aaa cgc aag cac cat          241
His Pro Gly Ser His Lys Val Pro Phe Phe Arg Lys Arg Lys His His
                 65                  70                  75 acc tgt cct tgc tca ccc aac ctg ctg tgc tcc agg ttc cca gac ggc          289
Thr Cys Pro Cys Ser Pro Asn Leu Leu Cys Ser Arg Phe Pro Asp Gly
             80                  85                  90
```

```
agg tac cgc tgc tcc atg gac ttg aag aac atc aat ttt ta ggcgcttgcc    340
Arg Tyr Arg Cys Ser Met Asp Leu Lys Asn Ile Asn Phe
         95                 100                 105 gggtctcagg ataccacca tccttttccc cagcactgcc tggatttta tttgtgccat       400
gcaacccagc tcctgtgact cttccagtcc ctacgctgac tactttgatc tctcttgcct    460
agtacacaca tatgcacaca gggagacata cctcccatca tgacgtggtc cccaggctgg    520
cctgacgatg tcccagcttg gagctgtggt gtgagagatg ccagcctgg ttcccttccc     580
tgcttaggct gccagagagg tggtaaatgg cagagaggac attccccctc ccctcccttc    640
ctgggcctgc tctccttcct ggccctgtc cctctcccca catgtacccc gcggtctgaa     700
ttggacattc ctggcacagg ctcttgggtg cattgtgggc acaggctctt gggtgcattg    760
aa                                                                   762
```

```
<210> SEQ ID NO 30
<211> LENGTH: 105
<212> TYPE: PRT
<213> ORGANISM: Macaca mulatta

<400> SEQUENCE: 30

Met Arg Gly Ala Thr Leu Val Ser Ile Met Phe Leu Leu Val Thr Val
 1               5                  10                  15

Ser Asp Cys Ala Val Ile Thr Gly Ala Cys Glu Arg Asp Val Gln Cys
            20                  25                  30

Gly Ala Gly Thr Cys Cys Ala Ile Ser Leu Trp Leu Arg Gly Leu Arg
        35                  40                  45

Met Cys Thr Pro Leu Gly Arg Glu Gly Glu Glu Cys His Pro Gly Ser
    50                  55                  60

His Lys Val Pro Phe Phe Arg Lys Arg Lys His Thr Cys Pro Cys
65                  70                  75                  80

Ser Pro Asn Leu Leu Cys Ser Arg Phe Pro Asp Gly Arg Tyr Arg Cys
                85                  90                  95

Ser Met Asp Leu Lys Asn Ile Asn Phe
            100                 105
```

```
<210> SEQ ID NO 31
<211> LENGTH: 105
<212> TYPE: PRT
<213> ORGANISM: Homo sapiens

<400> SEQUENCE: 31

Met Arg Gly Ala Thr Arg Val Ser Ile Met Leu Leu Val Thr Val
 1               5                  10                  15

Ser Asp Cys Ala Val Ile Thr Gly Ala Cys Glu Arg Asp Val Gln Cys
            20                  25                  30

Gly Ala Gly Thr Cys Cys Ala Ile Ser Leu Trp Leu Arg Gly Leu Arg
        35                  40                  45

Met Cys Thr Pro Leu Gly Arg Glu Gly Glu Glu Cys His Pro Gly Ser
    50                  55                  60

His Lys Val Pro Phe Phe Arg Lys Arg Lys His Thr Cys Pro Cys
65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105
```

<210> SEQ ID NO 32
<211> LENGTH: 27
<212> TYPE: DNA
<213> ORGANISM: Artificial Sequence
<220> FEATURE:
<223> OTHER INFORMATION: primer

<400> SEQUENCE: 32
cagatggaga ccaccatggg gttcatg     27

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
ttattttagt ctgatgcagt ccacctcttc     30

<210> SEQ ID NO 34
<211> LENGTH: 1182
<212> TYPE: DNA
<213> ORGANISM: Macaca mullatta
<220> FEATURE:
<221> NAME/KEY: CDS
<222> LOCATION: (1)...(1182)

<400> SEQUENCE: 34

```
atg gag acc acc atg ggg ttc atg gat gac aat gcc acc aac acc tcc      48
Met Glu Thr Thr Met Gly Phe Met Asp Asp Asn Ala Thr Asn Thr Ser
  1               5                  10                  15 acc agc ttc ctt tct gcg ctc aac cct cat gga gcc cat gcc gct tcc      96
Thr Ser Phe Leu Ser Ala Leu Asn Pro His Gly Ala His Ala Ala Ser
             20                  25                  30 ttc cca ttc aac ttc agc tat ggt gac tat gat atg cct ttg gat gaa     144
Phe Pro Phe Asn Phe Ser Tyr Gly Asp Tyr Asp Met Pro Leu Asp Glu
         35                  40                  45 gat gag gat gtg acc aat tcc cgg aca ttc ttt gct gcc aag att gtc     192
Asp Glu Asp Val Thr Asn Ser Arg Thr Phe Phe Ala Ala Lys Ile Val
     50                  55                  60 att ggg atg gcc ctg gtg ggc atc atg ctg gtc tgt ggc att ggc aac     240
Ile Gly Met Ala Leu Val Gly Ile Met Leu Val Cys Gly Ile Gly Asn
 65                  70                  75                  80 ttc gtc ttt atc gct gct ctg gtc cgc tac aag aaa ctg cgc aat ctc     288
Phe Val Phe Ile Ala Ala Leu Val Arg Tyr Lys Lys Leu Arg Asn Leu
                 85                  90                  95 acc aac ctg ctc atc gcc aac ctg gcc atc tcg gat ttc ctg gtg gcc     336
Thr Asn Leu Leu Ile Ala Asn Leu Ala Ile Ser Asp Phe Leu Val Ala
            100                 105                 110 att gtc tgc tgc ccc ttt gag atg gac tac tat gtg gtg cgc cag ctc     384
Ile Val Cys Cys Pro Phe Glu Met Asp Tyr Tyr Val Val Arg Gln Leu
        115                 120                 125 tcc tgg gag cac ggc cac atc ctg tgc acc tct gtc aac tac ctg cgc     432
Ser Trp Glu His Gly His Ile Leu Cys Thr Ser Val Asn Tyr Leu Arg
    130                 135                 140 act gtc tct ctc tat gtc tcc acc aat gcc ctg ctg gcc atc gcc att     480
Thr Val Ser Leu Tyr Val Ser Thr Asn Ala Leu Leu Ala Ile Ala Ile
145                 150                 155                 160 gac agg tat ctg gct att gtc cac ccg ctg aga cca cgg atg aag tgc     528
Asp Arg Tyr Leu Ala Ile Val His Pro Leu Arg Pro Arg Met Lys Cys
                165                 170                 175 caa aca gcc act ggc ctg att gcc ttg gtg tgg acg gtg tcc atc ctg     576
Gln Thr Ala Thr Gly Leu Ile Ala Leu Val Trp Thr Val Ser Ile Leu
```

```
Gln Thr Ala Thr Gly Leu Ile Ala Leu Val Trp Thr Val Ser Ile Leu
            180                 185                 190 atc gcc atc cct tcc gcc tac ttc acc acc gag acg gtc ctc gtc att      624
Ile Ala Ile Pro Ser Ala Tyr Phe Thr Thr Glu Thr Val Leu Val Ile
            195                 200                 205 gtc agg agc cag gaa aag atc ttc tgc ggc cag atc tgg cct gtt gac      672
Val Arg Ser Gln Glu Lys Ile Phe Cys Gly Gln Ile Trp Pro Val Asp
        210                 215                 220 cag cag ctg tac tac aag tcc tac ttc ctc ttt atc ttt ggc att gag      720
Gln Gln Leu Tyr Tyr Lys Ser Tyr Phe Leu Phe Ile Phe Gly Ile Glu
225                 230                 235                 240 ttc gtg ggc ccc gtg ttc acc atg acc ctg tgc tat gcc agg atc tcc      768
Phe Val Gly Pro Val Phe Thr Met Thr Leu Cys Tyr Ala Arg Ile Ser
                245                 250                 255 cgg gag ctc tgg ttc aag gcg gtc cct gga ttc cag acc gag cag atc      816
Arg Glu Leu Trp Phe Lys Ala Val Pro Gly Phe Gln Thr Glu Gln Ile
            260                 265                 270 cgc aag agg ctg cgc tgc cgc agg aag acg gtc ctg gtg ctt atg tgc      864
Arg Lys Arg Leu Arg Cys Arg Arg Lys Thr Val Leu Val Leu Met Cys
        275                 280                 285 atc ctc acc gcc tac gtg ctg tgc tgg gcg ccc ttc tac ggc ttc acc      912
Ile Leu Thr Ala Tyr Val Leu Cys Trp Ala Pro Phe Tyr Gly Phe Thr
290                 295                 300 atc gtg cgc gac ttc ttc ccc acc gtg ttc gtg aag gag aag cac tac      960
Ile Val Arg Asp Phe Phe Pro Thr Val Phe Val Lys Glu Lys His Tyr
305                 310                 315                 320 ctc act gcc ttc tac atc gtc gag tgc atc gcc atg agc aac agc atg     1008
Leu Thr Ala Phe Tyr Ile Val Glu Cys Ile Ala Met Ser Asn Ser Met
                325                 330                 335 atc aac acc ctg tgc ttc gtg aca gtc aag aac aac acc gcc aag tac     1056
Ile Asn Thr Leu Cys Phe Val Thr Val Lys Asn Asn Thr Ala Lys Tyr
            340                 345                 350 ttc aaa aag atc atg ctg ctc cac tgg aag gct tct tac aat ggc ggt     1104
Phe Lys Lys Ile Met Leu Leu His Trp Lys Ala Ser Tyr Asn Gly Gly
        355                 360                 365 aag tcc agt gca gac ctg gac ctc aag aca atc ggg atg cct gcc act     1152
Lys Ser Ser Ala Asp Leu Asp Leu Lys Thr Ile Gly Met Pro Ala Thr
370                 375                 380 gaa gag gtg gac tgc atc aga cta aaa taa                             1182
Glu Glu Val Asp Cys Ile Arg Leu Lys *
385                 390

<210> SEQ ID NO 35
<211> LENGTH: 393
<212> TYPE: PRT
<213> ORGANISM: Macaca mullatta

<400> SEQUENCE: 35

Met Glu Thr Thr Met Gly Phe Met Asp Asp Asn Ala Thr Asn Thr Ser
1               5                   10                  15

Thr Ser Phe Leu Ser Ala Leu Asn Pro His Gly Ala His Ala Ala Ser
            20                  25                  30

Phe Pro Phe Asn Phe Ser Tyr Gly Asp Tyr Asp Met Pro Leu Asp Glu
        35                  40                  45

Asp Glu Asp Val Thr Asn Ser Arg Thr Phe Phe Ala Ala Lys Ile Val
    50                  55                  60

Ile Gly Met Ala Leu Val Gly Ile Met Leu Val Cys Gly Ile Gly Asn
65                  70                  75                  80

Phe Val Phe Ile Ala Ala Leu Val Arg Tyr Lys Lys Leu Arg Asn Leu
```

```
                     85                  90                  95
Thr Asn Leu Leu Ile Ala Asn Leu Ala Ile Ser Asp Phe Leu Val Ala
                100                 105                 110

Ile Val Cys Cys Pro Phe Glu Met Asp Tyr Tyr Val Arg Gln Leu
            115                 120                 125

Ser Trp Glu His Gly His Ile Leu Cys Thr Ser Val Asn Tyr Leu Arg
        130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Thr Gly Leu Ile Ala Leu Val Trp Thr Val Ser Ile Leu
            180                 185                 190

Ile Ala Ile Pro Ser Ala Tyr Phe Thr Thr Glu Thr Val Leu Val Ile
            195                 200                 205

Val Arg Ser Gln Glu Lys Ile Phe Cys Gly Gln Ile Trp Pro Val Asp
            210                 215                 220

Gln Gln Leu Tyr Tyr Lys Ser Tyr Phe Leu Phe Ile Phe Gly Ile Glu
225                 230                 235                 240

Phe Val Gly Pro Val Phe Thr Met Thr Leu Cys Tyr Ala Arg Ile Ser
                245                 250                 255

Arg Glu Leu Trp Phe Lys Ala Val Pro Gly Phe Gln Thr Glu Gln Ile
            260                 265                 270

Arg Lys Arg Leu Arg Cys Arg Arg Lys Thr Val Leu Val Leu Met Cys
            275                 280                 285

Ile Leu Thr Ala Tyr Val Leu Cys Trp Ala Pro Phe Tyr Gly Phe Thr
            290                 295                 300

Ile Val Arg Asp Phe Phe Pro Thr Val Phe Val Lys Glu Lys His Tyr
305                 310                 315                 320

Leu Thr Ala Phe Tyr Ile Val Glu Cys Ile Ala Met Ser Asn Ser Met
                325                 330                 335

Ile Asn Thr Leu Cys Phe Val Thr Val Lys Asn Asn Thr Ala Lys Tyr
            340                 345                 350

Phe Lys Lys Ile Met Leu Leu His Trp Lys Ala Ser Tyr Asn Gly Gly
            355                 360                 365

Lys Ser Ser Ala Asp Leu Asp Leu Lys Thr Ile Gly Met Pro Ala Thr
            370                 375                 380

Glu Glu Val Asp Cys Ile Arg Leu Lys
385                 390

<210> SEQ ID NO 36
<211> LENGTH: 393
<212> TYPE: PRT
<213> ORGANISM: Homo sapiens

<400> SEQUENCE: 36

Met Glu Thr Thr Met Gly Phe Met Asp Asp Asn Ala Thr Asn Thr Ser
1               5                   10                  15

Thr Ser Phe Leu Ser Val Leu Asn Pro His Gly Ala His Ala Thr Ser
            20                  25                  30

Phe Pro Phe Asn Phe Ser Tyr Ser Asp Tyr Asp Met Pro Leu Asp Glu
        35                  40                  45

Asp Glu Asp Val Thr Asn Ser Arg Thr Phe Phe Ala Ala Lys Ile Val
50                  55                  60
```

```
Ile Gly Met Ala Leu Val Gly Ile Met Leu Val Cys Gly Ile Gly Asn
 65                  70                  75                  80

Phe Ile Phe Ile Ala Ala Leu Val Arg Tyr Lys Lys Leu Arg Asn Leu
                 85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
            115                 120                 125

Ser Trp Glu His Gly His Val Leu Cys Thr Ser Val Asn Tyr Leu Arg
130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Thr Gly Leu Ile Ala Leu Val Trp Thr Val Ser Ile Leu
            180                 185                 190

Ile Ala Ile Pro Ser Ala Tyr Phe Thr Thr Glu Thr Val Leu Val Ile
            195                 200                 205

Val Lys Ser Gln Glu Lys Ile Phe Cys Gly Gln Ile Trp Pro Val Asp
210                 215                 220

Gln Gln Leu Tyr Tyr Lys Ser Tyr Phe Leu Phe Ile Phe Gly Ile Glu
225                 230                 235                 240

Phe Val Gly Pro Val Val Thr Met Thr Leu Cys Tyr Ala Arg Met Thr
                245                 250                 255

Arg Glu Leu Trp Phe Lys Ala Val Pro Gly Phe Gln Thr Glu Gln Ile
            260                 265                 270

Arg Lys Arg Leu Arg Cys Arg Arg Lys Thr Val Leu Val Leu Met Cys
            275                 280                 285

Ile Leu Thr Ala Tyr Val Leu Cys Trp Ala Pro Phe Tyr Gly Phe Thr
290                 295                 300

Ile Val Arg Asp Phe Phe Pro Thr Val Phe Val Lys Glu Lys His Tyr
305                 310                 315                 320

Leu Thr Ala Phe Tyr Ile Val Glu Cys Ile Ala Met Ser Asn Ser Met
                325                 330                 335

Ile Asn Thr Leu Cys Phe Val Thr Val Lys Asn Asp Thr Val Lys Tyr
            340                 345                 350

Phe Lys Lys Ile Met Leu Leu His Trp Lys Ala Ser Tyr Asn Gly Gly
            355                 360                 365

Lys Ser Ser Ala Asp Leu Asp Leu Lys Thr Ile Gly Met Pro Ala Thr
370                 375                 380

Glu Glu Val Asp Cys Ile Arg Leu Lys
385                 390

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
ggcgccatga ggagcctgtg ctgc                                    24
```